United States Patent
Lewis et al.

(10) Patent No.: US 7,144,553 B2
(45) Date of Patent: *Dec. 5, 2006

(54) USE OF AN ARRAY OF POLYMERIC SENSORS OF VARYING THICKNESS FOR DETECTING ANALYTES IN FLUIDS

(75) Inventors: Nathan S. Lewis, La Canada, CA (US); Erik J. Severin, Pasadena, CA (US); Michael Freund, Altadena, CA (US); Adam J. Matzger, Pasadena, CA (US)

(73) Assignee: The California Institute of Technology, Pasadena, CA (US)

( * ) Notice: Subject to any disclaimer, the term of this patent is extended or adjusted under 35 U.S.C. 154(b) by 356 days.

This patent is subject to a terminal disclaimer.

(21) Appl. No.: 10/651,917

(22) Filed: Aug. 29, 2003

(65) Prior Publication Data

US 2004/0042933 A1    Mar. 4, 2004

Related U.S. Application Data

(60) Continuation of application No. 09/910,243, filed on Jul. 20, 2001, now Pat. No. 6,759,010, which is a division of application No. 09/442,074, filed on Nov. 16, 1999, now Pat. No. 6,387,329.

(60) Provisional application No. 60/108,915, filed on Nov. 17, 1998, provisional application No. 60/108,674, filed on Nov. 16, 1998.

(51) Int. Cl.
*G01N 27/02*    (2006.01)
(52) U.S. Cl. .............................. 422/82.02; 422/82.01; 422/83; 422/98; 204/400; 204/406; 204/411; 204/412; 204/431

(58) Field of Classification Search ............... 422/68.1, 422/82.01, 82.02, 82.03, 98; 436/149, 150; 204/406, 415, 418; 427/2.1, 2.11, 421, 427, 427/429

See application file for complete search history.

(56) References Cited

U.S. PATENT DOCUMENTS

| | | | |
|---|---|---|---|
| 3,677,071 A | 7/1972 | Martin | |
| 4,172,721 A | 10/1979 | Byrne | |
| 4,424,487 A | 1/1984 | Lauffer | |
| 4,674,320 A | 6/1987 | Hirschfeld | |
| 4,719,423 A | 1/1988 | Vinegar et al. | |
| 4,914,608 A | 4/1990 | LeBihan et al. | |
| 5,159,829 A | 11/1992 | Mayer et al. | |
| 5,212,447 A | 5/1993 | Paltiel | |
| 5,278,501 A | 1/1994 | Guilfoyle | |
| 5,286,414 A | 2/1994 | Kampf et al. | |

(Continued)

OTHER PUBLICATIONS

Bodenhöfer et al., "Chiral Discrimination by Simple Gas Sensors," Transducers, 1997 International Conference on Solid-State Sensors and Actuators, Digest of Technical Papers, Transduces 97, Chicago, IL, Jun. 16-19, 1997, vol. 2, pp. 1391-1394.

(Continued)

*Primary Examiner*—Jill Warden
*Assistant Examiner*—Dwayne K. Handy
(74) *Attorney, Agent, or Firm*—Buchannan Ingersoll & Rooney LLP

(57) ABSTRACT

Chemical sensors for detecting the activity of a molecule or analyte of interest is provided. The chemical sensors comprise and array or plurality of sensors that are capable of interacting with a molecule of interest, wherein the interaction provides a response fingerprint. The fingerprint can be associated with a library of similar molecules of interest to determine the molecule's activity and diffusion coefficient.

5 Claims, 10 Drawing Sheets

U.S. PATENT DOCUMENTS

| | | | |
|---|---|---|---|
| 5,302,274 | A | 4/1994 | Tomantschger et al. |
| 5,335,555 | A | 8/1994 | Guizot et al. |
| 5,425,869 | A | 6/1995 | Noding et al. |
| 5,466,348 | A | 11/1995 | Holm-Kennedy |
| 5,505,093 | A | 4/1996 | Giedd et al. |
| 5,512,882 | A | 4/1996 | Stetter et al. |
| 5,571,401 | A | 11/1996 | Lewis et al. |
| 5,591,898 | A | 1/1997 | Mayer |
| 5,627,329 | A | 5/1997 | Krishnan et al. |
| 5,698,089 | A | 12/1997 | Lewis et al. |
| 5,705,265 | A | 1/1998 | Clough et al. |
| 5,788,833 | A | 8/1998 | Lewis et al. |
| 5,804,100 | A | 9/1998 | Angelopoulos et al. |
| 5,876,577 | A | 3/1999 | McAleer et al. |
| 5,879,827 | A | 3/1999 | Debe et al. |
| 5,891,398 | A | 4/1999 | Lewis et al. |
| 5,911,872 | A | 6/1999 | Lewis et al. |
| 5,913,235 | A | 6/1999 | Silenius et al. |
| 5,951,846 | A | 9/1999 | Lewis et al. |
| 5,958,787 | A | 9/1999 | Schonfeld et al. |
| 5,959,191 | A | 9/1999 | Lewis et al. |
| 5,980,723 | A | 11/1999 | Runge-Marchese et al. |
| 6,023,163 | A | 2/2000 | Flaum et al. |
| 6,103,033 | A | 8/2000 | Say et al. |
| 6,134,461 | A | 10/2000 | Say et al. |
| 6,134,950 | A | 10/2000 | Forster et al. |
| 6,170,318 | B1 | 1/2001 | Lewis |
| 6,234,004 | B1 | 5/2001 | Revsbech et al. |
| 6,290,911 | B1 | 9/2001 | Lewis et al. |
| 6,305,214 | B1 | 10/2001 | Schattke et al. |
| 6,350,369 | B1 | 2/2002 | Lewis et al. |
| 6,387,329 | B1 * | 5/2002 | Lewis et al. .................. 422/98 |
| 6,610,367 | B1 * | 8/2003 | Lewis et al. .................. 427/58 |
| 6,759,010 | B1 * | 7/2004 | Lewis et al. ............. 422/82.02 |

OTHER PUBLICATIONS

Bodenhöfer et al., "Performances of Mass-Sensitive Devices for Gas Sensing: Thickness Shear Mode and Surface Acoustic Wave Transducers," Anal. Chem., 1996, 68, pp. 2210-2218.

Jiang et al., "Preparation and Properties of Organic Polymer Sub-Micrometer Function Films," *Electrets*, 1996, 9th International Symposium on Shanghai, China, Sep. 25-30, 1996, NY, pp. 678-683.

Stussi et al., "Chemoresistive conducting polymer-based odour sensors; influence of thickness changes on their sensing properties", *Sensors and Actuators B*, 43 (1997) pp. 180-185.

Dickinson et al., "Generating Sensor Diversity Through Combinatorial Polymer Synthesis" Anal. Cham. 1997, vol. 69, pp. 3413-3418.

Doleman et al., "Quantitative Study of the Resolving Power of Arrays of Carbon Black-Polymer Composites in Various Vapor-Sensing Tasks" Anal. Chem. 1998, 4177-4190.

Lipman, "E-noses nose out traditional odor-detection equipment" EDN magazine, Dec. 17, 1998.

Luinge et al., "Trace-level identity confirmation from infrared spectra by library searching and artificial neural networks" Analytica Chimica Acta 345 (1997) 173-184.

* cited by examiner

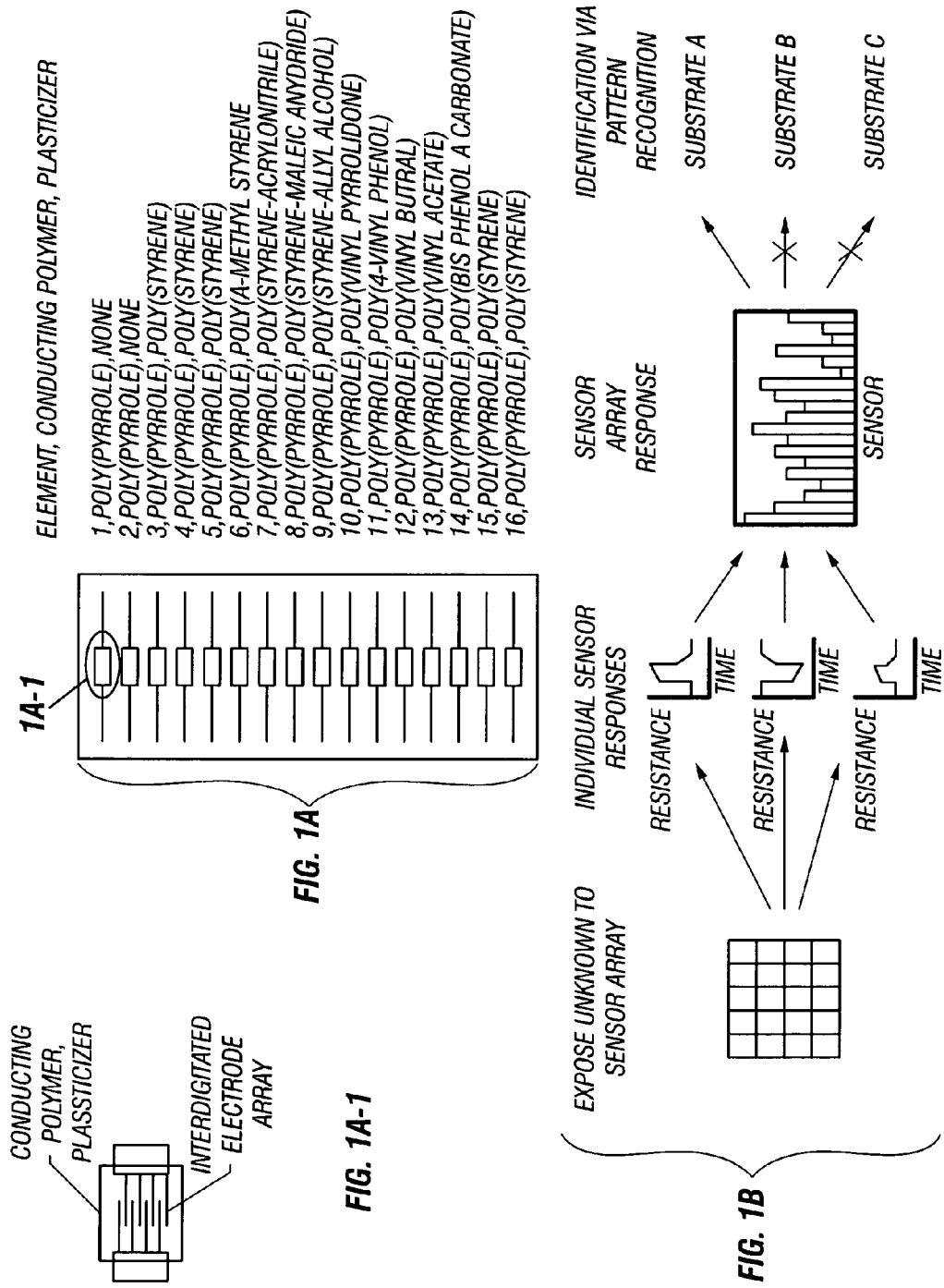

| alcohol | experiment al pI$_{50}$ | run # (bubbler #) | sensor # polymer name: poly(4-vinylpyridine) 1 | poly(vinyl chloride) 2 | poly(ethylene oxide) 3 |
|---|---|---|---|---|---|
| 1-butanol | -0.05 | 1 (8) | 0.23 (0.08) | 0.01 (0.15) | 1.83 (0.22) |
| 1-heptanol | 0.68 | 2 (6) | 0.05 (0.10) | 0.04 (0.16) | 1.90 (0.10) |
| 1-hexanol | 0.54 | 3 (6) | 0.09 (0.08) | 0.03 (0.16) | 1.76 (0.04) |
| 1-pentanol | 0.27 | 3 (7) | 0.17 (0.10) | -0.03 (0.13) | 1.63 (0.02) |
| 1-propanol | -0.48 | 3 (3) | 0.55 (0.14) | -0.03 (0.19) | 1.18 (0.01) |
| 2,4-dimethyl-3-pentanol | -1.38 | 2 (1) | 0.05 (0.14) | -0.02 (0.13) | 2.00 (0.06) |
| 2-butanol | -0.35 | 2 (8) | 0.20 (0.13) | -0.06 (0.12) | 1.35 (0.04) |
| 2-heptanol | 0.25 | 1 (2) | 0.13 (0.08) | -0.04 (0.09) | 2.89 (0.54) |
| 2-hexanol | 0.15 | 2 (2) | 0.16 (0.15) | 0.01 (0.15) | 1.69 (0.09) |
| 2-methyl-1-butanol | -0.15 | 2 (7) | 0.04 (0.11) | 0.02 (0.12) | 1.74 (0.05) |
| 2-methyl-1-propanol | -0.39 | 1 (6) | 0.12 (0.07) | 0.01 (0.12) | 1.84 (0.15) |
| 2-methyl-3-pentanol | -0.89 | 1 (1) | 0.13 (0.09) | 0.06 (0.11) | 2.34 (0.33) |
| 2-pentanol | -0.07 | 3 (8) | 0.06 (0.06) | -0.03 (0.13) | 1.41 (0.02) |
| 2-propanol | -0.47 | 1 (7) | 0.24 (0.08) | 0.13 (0.14) | 1.58 (0.23) |
| 3-hexanol | -0.47 | 3 (1) | 0.07 (0.08) | 0.01 (0.13) | 1.57 (0.03) |
| 3-methyl-1-butanol | -0.19 | 3 (5) | 0.08 (0.08) | 0.03 (0.08) | 1.49 (0.02) |
| 3-pentanol | -0.37 | 2 (4) | 0.11 (0.09) | 0.08 (0.15) | 1.52 (0.04) |
| ethanol | -1.10 | 2 (3) | 1.52 (0.15) | 0.19 (0.14) | 1.08 (0.02) |
| methanol | -3.09 | 1 (3) | 3.71 (0.23) | 0.57 (0.12) | 1.33 (0.10) |
| neopentanol (solid) | -0.67 | 3 (2) | 0.03 (0.10) | 0.00 (0.18) | 1.37 (0.04) |
| benzyl alcohol | 0.32 | 1 (4) | 0.06 (0.07) | 0.04 (0.13) | 3.05 (0.91) |
| tert-amyl alcohol | -2.56 | 1 (5) | 0.10 (0.10) | -0.07 (0.14) | 1.77 (0.24) |
| 1,3-propanediol | -1.87 | 3 (4) | -0.02 (0.10) | 0.04 (0.12) | 0.17 (0.02) |
| 1,4-butanediol | -1.41 | 2 (5) | -0.01 (0.09) | -0.01 (0.15) | 0.19 (0.20) |

FIG. 5A

| poly(styrene/allyl alcohol) | poly(4-vinylphenol) | poly(vinyl acetate) | etethyl cellulose | poly(N-vinylpyrrolidone) |
|---|---|---|---|---|
| 4 | 5 | 6 | 7 | 8 |
| 0.56 (0.08) | 0.41 (0.17) | 0.11 (0.08) | 4.04 (0.20) | 0.31 (0.70) |
| 0.23 (0.02) | 0.08 (0.11) | -0.07 (0.05) | 4.28 (0.21) | 0.52 (0.84) |
| 0.45 (0.05) | 0.11 (0.09) | -0.08 (0.05) | 5.32 (0.18) | -0.07 (0.60) |
| 0.58 (0.05) | 0.16 (0.10) | 0.02 (0.04) | 4.97 (0.14) | 0.67 (0.58) |
| 0.57 (0.04) | 0.70 (0.09) | 0.20 (0.03) | 3.17 (0.14) | 1.08 (0.82) |
| 0.17 (0.02) | 0.10 (0.11) | 0.00 (0.03) | 4.94 (0.25) | 0.11 (0.61) |
| 0.65 (0.10) | 0.29 (0.23) | 0.14 (0.05) | 3.89 (0.29) | 0.23 (0.68) |
| 0.28 (0.04) | 0.11 (0.13) | -0.09 (0.05) | 4.76 (0.18) | 0.23 (0.99) |
| 0.37 (0.03) | 0.17 (0.11) | -0.05 (0.03) | 5.10 (0.31) | 0.77 (0.42) |
| 0.34 (0.04) | 0.16 (0.14) | -0.01 (0.04) | 4.76 (0.27) | 0.09 (0.73) |
| 0.48 (0.08) | 0.28 (0.14) | 0.10 (0.03) | 3.98 (0.20) | 0.47 (0.59) |
| 0.29 (0.05) | 0.19 (0.11) | -0.03 (0.04) | 5.24 (0.26) | 0.76 (0.61) |
| 0.57 (0.07) | 0.14 (0.09) | 0.00 (0.07) | 4.90 (0.19) | 0.68 (0.55) |
| 0.57 (0.06) | 0.62 (0.17) | 0.14 (0.06) | 3.31 (0.31) | 0.40 (0.88) |
| 0.40 (0.04) | 0.07 (0.08) | -0.06 (0.05) | 5.56 (0.23) | 0.02 (1.03) |
| 0.39 (0.03) | 0.07 (0.07) | 0.01 (0.04) | 4.82 (0.13) | 0.08 (0.83) |
| 0.55 (0.06) | 0.16 (0.13) | -0.01 (0.05) | 4.83 (0.41) | -0.13 (0.81) |
| 0.59 (0.05) | 2.19 (0.17) | 0.31 (0.03) | 2.19 (0.14) | 4.03 (0.74) |
| 0.55 (0.03) | 2.51 (0.21) | 0.40 (0.07) | 1.82 (0.22) | 7.76 (0.78) |
| 0.14 (0.03) | -0.01 (0.05) | 0.02 (0.03) | 3.28 (0.20) | -0.13 (0.79) |
| | | | | |
| 0.22 (0.03) | 0.10 (0.07) | -0.03 (0.05) | 2.07 (1.01) | -0.10 (0.59) |
| 0.39 (0.07) | 0.26 (0.14) | 0.06 (0.05) | 3.91 (0.29) | 0.35 (0.62) |
| 0.06 (0.02) | -0.01 (0.05) | 0.01 (0.03) | 0.40 (0.19) | -0.39 (0.80) |
| 0.06 (0.06) | 0.04 (0.06) | -0.02 (0.04) | 0.81 (0.68) | -0.09 (0.79) |

FIG. 5B

| poly(ethylene/acrylic acid) | poly(ethylene/vinyl acetate) | poly(methyl methacrylate) | poly(methylvinylether/maleic anhydride) | 1,2-polybutadiene |
|---|---|---|---|---|
| 9 | 10 | 11 | 12 | 13 |
| 1.65 (0.14) | 0.74 (0.10) | 0.00 (0.02) | -0.01 (0.01) | 0.23 (0.10) |
| 1.66 (0.09) | 0.69 (0.04) | 0.01 (0.03) | 0.00 (0.01) | 0.30 (0.02) |
| 1.84 (0.05) | 0.73 (0.02) | 0.01 (0.03) | -0.01 (0.02) | 0.28 (0.01) |
| 1.70 (0.03) | 0.67 (0.01) | 0.01 (0.02) | 0.00 (0.02) | 0.21 (0.01) |
| 1.07 (0.02) | 0.40 (0.02) | 0.01 (0.03) | -0.02 (0.02) | -0.03 (0.01) |
| 2.49 (0.05) | 2.42 (0.09) | 0.02 (0.02) | 0.03 (0.02) | 1.19 (0.04) |
| 1.62 (0.03) | 0.76 (0.04) | 0.00 (0.03) | -0.02 (0.01) | 0.26 (0.01) |
| 1.91 (0.06) | 0.99 (0.04) | 0.00 (0.03) | 0.01 (0.03) | 0.45 (0.02) |
| 1.97 (0.05) | 0.92 (0.03) | -0.01 (0.02) | 0.10 (0.02) | 0.45 (0.01) |
| 1.82 (0.04) | 0.91 (0.03) | -0.01 (0.02) | -0.01 (0.01) | 0.41 (0.01) |
| 1.65 (0.10) | 0.78 (0.08) | 0.00 (0.02) | -0.04 (0.02) | 0.28 (0.07) |
| 2.17 (0.02) | 1.59 (0.04) | 0.00 (0.03) | 0.08 (0.02) | 0.75 (0.02) |
| 1.77 (0.02) | 0.82 (0.02) | -0.01 (0.02) | 0.00 (0.01) | 0.34 (0.01) |
| 1.45 (0.07) | 0.63 (0.04) | 0.00 (0.02) | -0.04 (0.03) | 0.16 (0.05) |
| 1.81 (0.04) | 1.07 (0.01) | 0.01 (0.02) | 0.01 (0.02) | 0.51 (0.01) |
| 1.77 (0.02) | 0.75 (0.02) | -0.01 (0.04) | -0.04 (0.02) | 0.36 (0.01) |
| 1.79 (0.03) | 1.03 (0.04) | -0.01 (0.01) | -0.01 (0.02) | 0.43 (0.01) |
| 0.78 (0.03) | 0.20 (0.04) | 0.14 (0.03) | -0.03 (0.02) | -0.13 (0.03) |
| 0.69 (0.03) | 0.15 (0.04) | 0.57 (0.03) | 0.52 (0.05) | -0.01 (0.01) |
| 1.54 (0.05) | 0.94 (0.03) | 0.00 (0.03) | 0.00 (0.02) | 0.42 (0.01) |
| 0.58 (0.34) | 0.33 (0.17) | -0.01 (0.02) | -0.04 (0.02) | 0.11 (0.08) |
| 2.05 (0.12) | 1.04 (0.08) | 0.00 (0.02) | -0.03 (0.02) | 0.47 (0.06) |
| 0.06 (0.01) | 0.02 (0.02) | -0.01 (0.04) | -0.03 (0.02) | 0.02 (0.01) |
| 0.14 (0.15) | 0.05 (0.05) | -0.01 (0.02) | -0.03 (0.02) | 0.03 (0.02) |

*FIG. 5C*

| poly(styrene/acrylonitrile) | poly(methyloctadecylsiloxane) | poly(vinyl butryal) | poly(ethylene glycol) | poly(2,4,6-tribromostyrene) | polystrene |
|---|---|---|---|---|---|
| 15 | 16 | 17 | 18 | 19 | 20 |
| 0.00 (0.00) | 0.42 (0.02) | 1.14 (0.27) | 2.37 (0.25) | 0.12 (0.06) | -0.46 (0.73) |
| 0.00 (0.00) | 0.41 (0.03) | 0.45 (0.22) | 1.23 (0.14) | 0.01 (0.02) | -0.01 (0.82) |
| 0.00 (0.00) | 0.49 (0.02) | 0.89 (0.14) | 1.79 (0.08) | 0.04 (0.03) | 0.23 (0.94) |
| 0.01 (0.00) | 0.46 (0.02) | 1.04 (0.18) | 1.95 (0.06) | 0.07 (0.06) | -0.21 (0.80) |
| 0.02 (0.00) | 0.28 (0.02) | 1.51 (0.20) | 2.12 (0.11) | 0.25 (0.04) | 0.47 (0.59) |
| 0.00 (0.01) | 0.72 (0.02) | 0.54 (0.21) | 1.85 (0.04) | 0.01 (0.02) | -0.29 (0.69) |
| 0.00 (0.00) | 0.40 (0.02) | 1.03 (0.23) | 1.95 (0.09) | 0.13 (0.02) | 0.17 (0.32) |
| 0.00 (0.00) | 0.49 (0.03) | 0.62 (0.19) | 2.13 (0.49) | 0.03 (0.01) | -0.03 (0.32) |
| 0.01 (0.00) | 0.51 (0.01) | 0.77 (0.21) | 1.73 (0.11) | 0.03 (0.02) | 0.08 (0.76) |
| 0.00 (0.01) | 0.45 (0.02) | 0.77 (0.24) | 2.08 (0.11) | 0.03 (0.03) | 0.15 (0.84) |
| 0.00 (0.00) | 0.41 (0.02) | 1.01 (0.21) | 2.41 (0.19) | 0.09 (0.05) | 0.20 (0.50) |
| 0.01 (0.00) | 0.59 (0.02) | 0.70 (0.20) | 2.34 (0.25) | 0.03 (0.03) | -0.09 (0.84) |
| 0.00 (0.00) | 0.45 (0.02) | 1.03 (0.28) | 1.85 (0.07) | 0.07 (0.05) | -0.12 (0.79) |
| 0.00 (0.00) | 0.36 (0.03) | 1.15 (0.17) | 2.34 (0.29) | 0.14 (0.04) | -0.04 (0.47) |
| 0.00 (0.00) | 0.53 (0.02) | 0.87 (0.20) | 1.63 (0.10) | 0.06 (0.08) | -0.12 (0.74) |
| 0.00 (0.00) | 0.42 (0.02) | 0.90 (0.12) | 1.85 (0.06) | 0.03 (0.03) | -0.09 (0.73) |
| 0.00 (0.00) | 0.50 (0.03) | 0.96 (0.31) | 1.85 (0.10) | 0.07 (0.04) | 0.14 (0.71) |
| 0.17 (0.01) | 0.23 (0.02) | 1.44 (0.25) | 2.14 (0.10) | 0.42 (0.04) | -0.11 (0.63) |
| 0.62 (0.03) | 0.21 (0.02) | 1.58 (0.25) | 2.78 (0.20) | 0.27 (0.03) | 0.11 (0.70) |
| 0.00 (0.00) | 0.34 (0.02) | 0.39 (0.20) | 1.75 (0.07) | 0.01 (0.03) | -0.21 (0.56) |

| | | | | | |
|---|---|---|---|---|---|
| 0.00 (0.00) | 0.17 (0.11) | 0.34 (0.26) | 1.36 (0.48) | 0.01 (0.04) | -0.50 (0.76) |
| 0.00 (0.00) | 0.46 (0.01) | 0.74 (0.16) | 2.26 (0.23) | 0.08 (0.03) | 0.09 (0.48) |
| 0.00 (0.00) | 0.01 (0.02) | 0.09 (0.18) | 0.09 (0.09) | 0.00 (0.13) | 0.04 (0.78) |
| 0.00 (0.01) | 0.04 (0.04) | 0.00 (0.14) | 0.13 (0.13) | 0.01 (0.03) | -0.32 (0.87) |

FIG. 5D

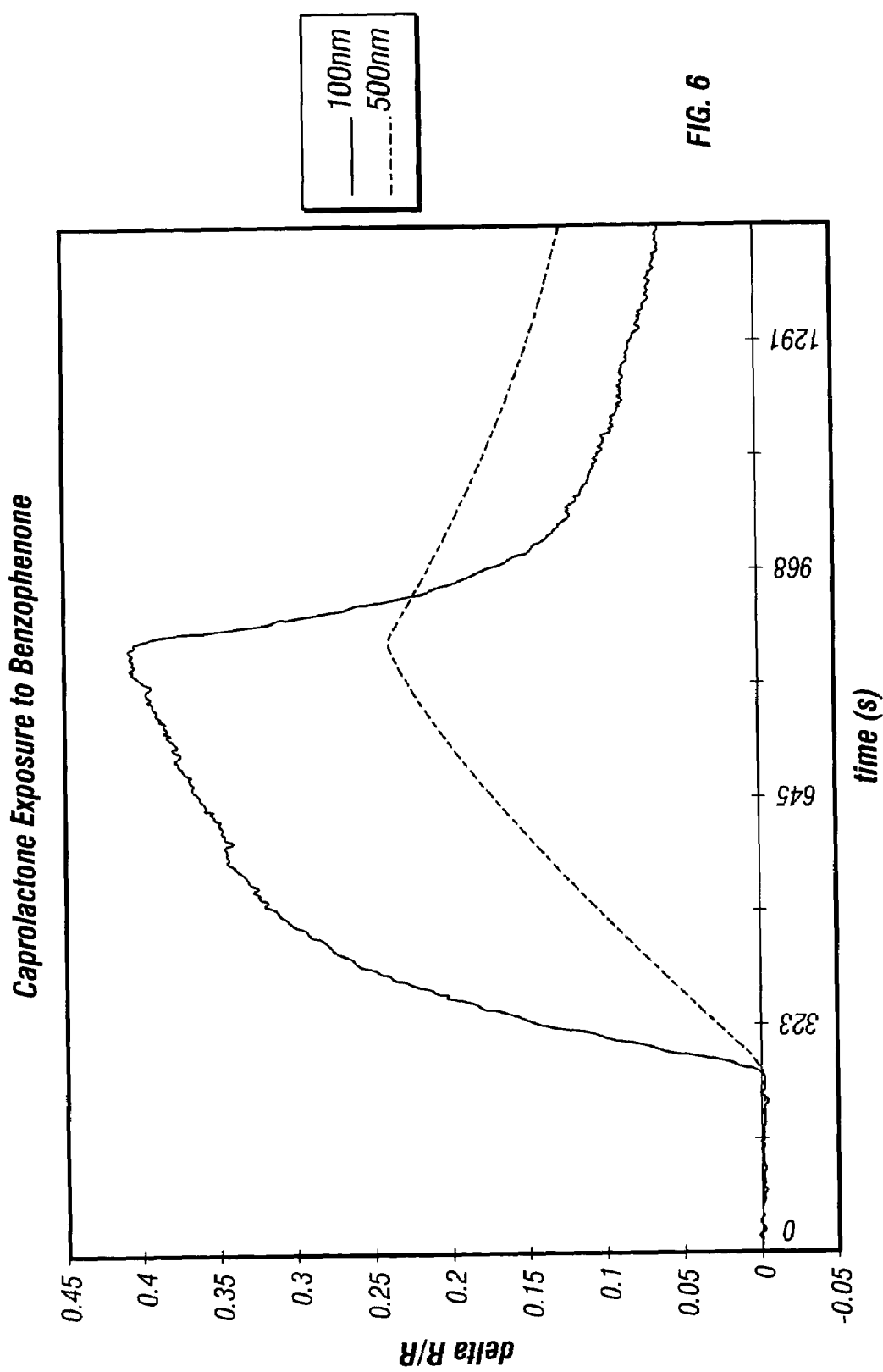

USE OF AN ARRAY OF POLYMERIC SENSORS OF VARYING THICKNESS FOR DETECTING ANALYTES IN FLUIDS

CROSS REFERENCE TO RELATED APPLICATIONS

This application is a continuation of Ser. No. 09/910,243 filed Jul. 20, 2001 now U.S. Pat No. 6,759,010, which is a divisional of U.S. application Ser. No. 09/442,074, filed Nov. 16, 1999 (now U.S. Pat. No. 6,387,329) which claims the benefit under 35 U.S.C. 119(e) of the U.S. Provisional Application No. 60/108,915, filed on Nov. 17, 1998 and U.S. Provisional Application No. 60/108,674, filed on Nov. 16, 1998, all of which are incorporated by reference.

STATEMENT AS TO FEDERALLY-SPONSORED RESEARCH

The U.S. Government has certain rights in this invention pursuant to Grant No. DAAK60-97-K-9503 awarded by DARPA and Grant No. DAAG55-97-1-0187 awarded by the U.S. Army.

FIELD OF THE INVENTION

This invention relates generally to sensors and sensor systems for detecting analytes in fluids and more particularly sensors having electrical properties that vary according to the presence and concentration of analytes, and to methods of using such sensor systems.

BACKGROUND OF THE INVENTION

There is considerable interest in developing sensors that act as analogs of the mammalian olfactory system (Lundstrom et al. (1991) Nature 352:47–50; Shurmer and Gardner (1992) Sens. Act. B 8:1–11; Shurmer and Gardner (1993) Sens. Actuators B 15:32). Prior attempts to produce a broadly responsive sensor array have exploited heated metal oxide thin film resistors (Gardner et al. (1991) Sens. Act. B4:117–121; Gardner et al. (1991) Sens. Act. B 6:71–75), polymer sorption layers on the surfaces of acoustic wave resonators (Grate and Abraham (1991) Sens. Act. B 3:85–111; Grate et al. (1993) Anal. Chem. 65:1868–1881), arrays of electrochemical detectors (Stetter et al. (1986) Anal. Chem. 58:860–866; Stetter et al. (1990) Sens. Act. B 1:43–47; Stetter et al. (1993) Anal. Chem. Acta 284:1–11), conductive polymers or composites that consist of regions of conductors and regions of insulating organic materials (Pearce et al. (1993) Analyst 118:371–377; Shurmer et al. (1991) Sens. Act. B 4:29–33; Doleman et al. (1998) Anal. Chem. 70:2560–2654; Lonergan et al. Chem. Mater. 1996, 8:2298). Arrays of metal oxide thin film resistors, typically based on tin oxide ($SnO_2$) films that have been coated with various catalysts, yield distinct, diagnostic responses for several vapors (Corcoran et al. (1993) Sens. Act. B 15:32–37). However, due to the lack of understanding of catalyst function, $SnO_2$ arrays do not allow deliberate chemical control of the response of elements in the arrays nor reproducibility of response from array to array. Surface acoustic wave resonators are extremely sensitive to both mass and acoustic impedance changes of the coatings in array elements, but the signal transduction mechanism involves somewhat complicated electronics, requiring frequency measurement to 1 Hz while sustaining a 100 MHZ Rayleigh wave in the crystal.

Although these sensors have particular advantages there exists a need for polymer based sensor system that shows intra-array variation without necessarily changing the polymer itself. Such a system would allow simultaneous determination of kinetic and equilibrium properties of an analyte. The present invention fulfills these and other needs.

SUMMARY OF THE INVENTION

Systematic variation in the thickness of a non-conducting, semi-conducting, and/or conductive organic material in a sensor of the invention has been performed and demonstrates that the time course of response to an analyte is different depending upon the thickness of the material film. In this way it is possible to combine rapid response times on the thinnest films in order to obtain quick information on the presence of an analyte as well as its identity, while simultaneously obtaining kinetic response information that allows measurement of the permeability of the analyte through the film, yielding information on the apparent diffusion coefficient as well as other important kinetic information on the properties of the analyte being detected by the sensors in the array. The elapsed time required to obtain the equilibrium constant information is therefore much shorter than would be the case if the analyte were sufficiently slow-diffusing that one had to acquire measurements on one non-conductive, semi-conductive and/or conductive organic material to determine both the time course and the final steady-state value. Use of an array of varying non-conductive, semi-conductive, and/or conductive organic material thickness would therefore yield information in a desired fashion.

Accordingly, the invention provides a method for identifying a molecule, the molecule's diffusion coefficient, the specific activity, structure and/or function of the molecule.

In one embodiment, the present invention provides a sensor, comprising regions of a first conductive material and a second material compositionally different than the first material, wherein the sensor provides an electrical path through the regions of the first conductive material and the regions of the second material, wherein the sensor comprises at least one region of second material having a different thickness than at least one other region of second material, the second material being selected from the group consisting of conductive organic material, semi-conductive material and non-conductive material. The thickness of the second material ranges from about 0.1 μm to about 100 μm, and typically about 0.1 μm to about 20 μm.

In another embodiment, the invention provides an array of sensors responsive to a molecule's physical, chemical, or biological characteristics. The array comprises a plurality of sensors, each sensor comprising regions of a first conductive material and a second material compositionally different than the first material, wherein the sensor provides an electrical path through the regions of the first conductive material and the regions of the second material, wherein the sensor comprises at least one region of second material having a different thickness than at least one other region of second material, the second material being selected from the group consisting of conductive organic material, semi-conductive material and non-conductive material.

The invention provides a broadly responsive analyte detection sensor array based on a variety of "chemiresistor" elements. Such elements are simply prepared and are readily modified chemically to respond to a broad range of analytes. In addition, these sensors yield a rapid, low-power, dc electrical signal in response to the analyte of interest, and their signals are readily integrated with software- or hardware-based algorithms including neural networks for purposes of analyte identification and physical, biological, chemical characteristics of the analyte.

In use, the sensors of the invention provide a change in resistance between the conductive elements when contacted with an analyte or molecule, which interacts second material (e.g., a material compositionally different than the first conductive material) of the sensor. The second material (e.g., a non-conductive material, semi-conductive material or conductive organic material) can be made of any material designed to interact or bind to a class, genus, or specie of analyte.

Also provided is a method for determining a physical, chemical, and/or biological characteristics of a molecule. The method uses a sensing device to produce a characteristic experimental pattern generated by a plurality sensors. The pattern has information on the molecular properties for a molecule or analyte of interest as well as information regarding the analyte's or molecule's diffusion coefficient data. A response pattern is produced for each member of the library. The response patterns may include a change in signal over a period of time. Such change in the pattern is indicative of the diffusion coefficient of a molecule or analyte. These patterns are then stored and associated with the library. The library contains patterns for molecules having a desired or known property or activity.

In one embodiment, a method is provided for screening samples for a specific activity or structure by measuring outputs of a plurality of sensors, each sensor, comprising regions of a first conductive material and a second material compositionally different than the first material wherein the sensor comprises at least one region of the second material having a different thickness than at least one other region of the second material in the plurality of sensor, and using results of said measuring to obtain a signal profile, relating to a change in resistance over time in the plurality of sensors; and comparing the signal profile to a previously-obtained signal profile indicating a standard sample having a specific activity, wherein the signal profile is indicative of a specific activity or a specific structure.

In another embodiment, the invention provides a method of determining the diffusion coefficient of an analyte, comprising contacting a sensor with the analtye, the sensor comprising, regions of a first conductive material and a second material compositionally different than the first material, wherein the sensor provides an electrical path through the regions of the first material and the regions of the second material, and wherein the sensor comprises at least one region of second material having a different thickness than at least one other region of second material, the second material being selected from the group consisting of a conductive organic material, a semi-conductive material and a non-conductive material; the sensors constructed to provide a first response when contacted with a first chemical analyte, and a second different response when contacted with a second different chemical analyte; and measuring a change in the sensor's response to the analyte over time, the change in response being indicative of the diffusion coefficient of the analyte.

In another embodiment, the invention provides a method of forming an electrically conductive polymer sensor, said method comprising, providing a polymer solution comprising at least a first conductive material and at least a second material, compositionally different than the first material in a solvent; providing a substrate; and applying the polymer solution to the substrate using a spray apparatus.

BRIEF DESCRIPTION OF THE DRAWING

These and other objects of the present invention will now be described in detail with reference to the accompanying drawing, in which:

FIGS. 5A–5D shows a table where the first three columns give the name of the alcohol, its experimental $pI_{50}$ value and run in which it was analyzed (and the bubbler in which it was placed). The remainder of the table lists the responses (expressed as percent change in electrical resistance relative to base line resistance) of the 19 different polymer/carbon black sensors upon exposure to the alcohols at 5% of their respective saturated vapor pressures. The standard deviation of the responses over ten trials are given in parenthesis. Sensor 14 was not functioning. The last four alcohols were not used in building the model.

FIG. 6 illustrates a response of a sensor array of the present invention.

DETAILED DESCRIPTION OF THE INVENTION

Figure 1C:
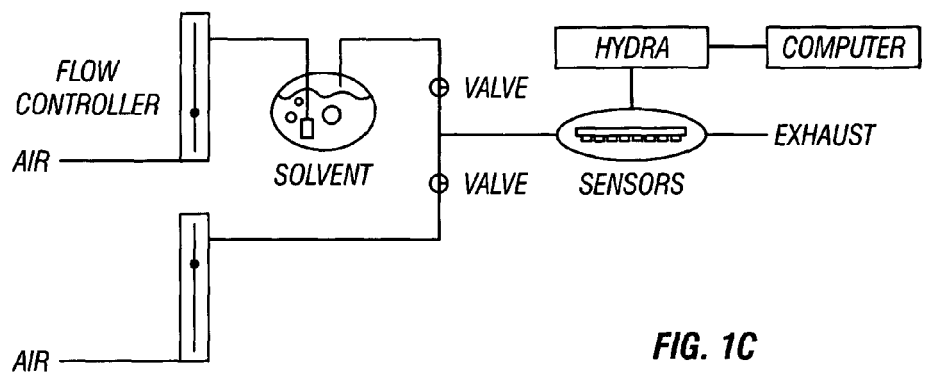
FIGS. 1A and 1A-1 shows an overview of sensor design; 1B, shows an overview of sensor operation; and 1C, shows an overview of system operation.

Studies have shown that certain materials are sensitive to a wide range of gases and vapors and can be used in gas-sensing microelectronic devices. In certain instances, a basic model for such a sensor comprises a thin uniform polymer film lying on top of a pair of coplanar electrodes supported by an insulating substrate. As the gas, or vapor, contact the sensor film it diffuses into the film and is adsorbed at sites randomly distributed throughout the film. The diffusion and adsorption equations can be presented in terms of several fundamental dimensionless parameters that describe the underlying chemical and physical properties of the system. (see, Gardner et al., *IEE Proc., Circuits Devices Syst.* 142, 321–33, (1995)).

Accordingly, the invention provides methods of determining a physical, chemical or biological property of a molecule or analyte of interest, including a molecule's or analyte's diffusion coefficient. In one embodiment, the invention measures the molecule's or analyte's interaction with a sensor over a period of time. The measuring can be performed using a parameter proportional to the molecule's concentration in the sample, determining the slope of the linear portion of that relationship, and multiplying that slope by a constant.

Measurements of Diffusion

Sensors that sorb analytes are used in a variety of detection schemes for sensing the presence of an analyte, for example, an analyte in a fluid. The sorption of polymers can be transduced into measurable signals through use of a surface acoustic wave crystal, a quartz microbalance resonator, a dye-impregnated polymeric coating on an optical fiber, bulk conducting organic materials, and addition of conductive fillers to insulating organic polymers to produce a change in electrical resistance of the composite films. Information about the type and quantity of an analyte in, for example, a fluid is contained both in the steady-state response to the presence of an analyte and in the time course of this response as it approaches its steady-state signal. The ability to obtain information on the type of, and quantity of, various analytes in fluids is enhanced by using both the temporal behavior as well as the steady-state behavior. However, when large numbers of sensors are present, it may not be feasible or convenient to record enough data points to obtain the required time course information from each of a large number of sensors. The need for collection of such data is obviated by using a collection of nominally identical sensors that differ not in composition, but in their thickness or other permeation properties, to the analyte of concern. Accordingly, measurements on the sensors that exhibit rapid permeation to analytes yield steady-state values while measurements at the approximately same time interval on films with poorer analyte permeation yields the desired diffusion coefficient data. In this way it is possible to combine rapid response times on the thinnest films in order to obtain quick information on the presence of an analyte as well as its identity, while simultaneously obtaining kinetic response information that allows measurement of the permeability of the analyte through the film, yielding information on the apparent diffusion coefficient as well as other important kinetic information on the properties of the analyte being detected by the sensors in the array. Thus, through relatively infrequent and slow measurements of the response of an array of such sensors of different thickness, information can be extracted regarding both the diffusion properties and the equilibrium binding properties of the desired analyte, therefore enhancing the performance of vapor detection apparatus.

A diffusion coefficient indicates the rate at which a molecule moves through a medium under a concentration gradient at a particular temperature and pressure. For example the diffusion of a chemical through a solid particulate is encountered in numerous industrial processes. Diffusion coefficients often must be known to properly design and operate these processes and are useful in determining additional physical characteristics of a sample. For example, in a polyethylene manufacturing process, polymerization occurs in a flammable hydrocarbon solvent such as hexane. After the polymerization, the hexane solvent must be separated and recovered from the polymer to provide a clean resin product. The resin, usually in a form of powder, must be dried to a very low level to minimize the emission of hexane to the environment and the risk of explosion due to hexane build-up in storage vessels. When the hexane in the polyethylene is below 5%, the drying process becomes essentially a process of hexane diffusion in the polymer. The diffusion coefficient therefore is needed to properly design and optimize the process. As another example, crude poly (vinyl chloride) resins usually contain vinyl chloride monomer, a carcinogen. Its diffusion coefficient is needed to determine the conditions required to reduce the toxic vinyl chloride monomer concentration to a safe level.

Most conventional methods of measuring the diffusion coefficient in a plastic material are based on a film permeability method similar to ASTM D 1434. In such a method, a film made of the plastic material is placed between two chambers, one of which holds a constant concentration of the sample to be tested. The sample permeates through the film into the other chamber and, by measuring the sample concentration in the second chamber, one can obtain the diffusion coefficient. Although this method can produce good precision and accuracy for many practical applications, it has serious shortcomings if casting a film changes the morphology and physicochemical characteristics (such as crystallinity) of the material and if data for unaltered particulates are desired. In addition, at high temperatures and pressures, the mechanical integrity of the film may become a problem.

The diffusion coefficient depends upon the temperature of the sample. The particles and the diffusion cell can be heated in an oven and the inert gas should preferably be heated to the same temperature as the particles.

As discussed herein, a calculation of the diffusion coefficient is a temporal physical process. Accordingly measurements must be obtained at different time points or during the course of a process of measurement. The two or more measurements give the parameter proportional to the concentration of the molecule in the sample for an interval of time. After a small initial time, the change in the natural log of the parameter per unit time (i.e., the slope of the plot of the natural log of GC area points versus time) will become constant. It is this constant or linear portion of the slope that is used to calculate the diffusion coefficient. The calculation is very simply made by multiplying the slope by a constant. For a spherical or near-spherical particle that constant is $-R^2/\pi^2$ where R is the average radius of a particle. If the particles are in the form of flakes the constant is $-4l^2/\pi^2$, where l is flake thickness, other geometries can be approximated by an equivalent radius using the constant for a spherical particle.

Accordingly, in one embodiment, the invention provides systems, methods and devices for simultaneously determining an equilibrium constant (i.e., partition coefficient) as well as a diffusion coefficient. In certain instances, a thinner polymer layer is used to determine the partition coefficient and rapid identification of an analyte, whereas a thicker polymer layer can then be used to determine a diffusion coefficient.

The partition coefficient, K, is defined as $K=C_s/C_v$, wherein $C_s$ is the concentration of analyte (solute) in a sorbent phase and $C_v$ is the concentration of the analyte in a vapor phase at equilibrium (at steady-state). In the experimental protocol used herein, $C_v$ is constant since the vapor generation apparatus is continuously replenishing the vapor stream.

Using a sensor of the invention, it is possible to concurrently or subsequently determine the diffusion coefficient of an analyte with respect to a particular polymer. As such, the present invention provides a method for measuring a diffusion coefficient of an analyte, comprising: contacting a first sensor having a first predetermined polymer thickness to elicit a first response; contacting a second sensor having a second predetermined polymer thickness to elicit a second response; comparing the first response to the second response to calculate a time lag and thereafter measuring the diffusion coefficient of the analyte.

In this aspect, it is assumed that the analyte and the polymer do not react. In the absence of a reaction between the analyte and the polymer, Fick's Law applies i.e., $$\frac{\partial C}{\partial t} = D\frac{\partial^2 C}{\partial x^2} \qquad \text{Equation I}$$

wherein C is the concentration of the analyte and D is the diffusivity. In order to measure the diffusivity experimentally in a polymer based sensor, the time lag procedure is used. Using this procedure, a plot of flux $(\Delta(\Delta R/R_i)/\Delta t)$ versus times yields a straight line whose intercept $\theta$ i.e., the time lag, on the t axis is represented by Equation II.

$$D = \frac{L^2}{6\theta} \qquad \text{Equation II}$$

From this graphical relationship the time lag $\theta$ is determined. $\Delta R$ is equal to $R_t - R_i$ wherein $R_t$ is the resistance at time t and $R_i$ is the initial resistance. L is the polymer thickness of the sensor (either predetermined or subsequently determined), the time lag $\theta$ is the t intercept and D is the diffusion coefficient.

The diffusion coefficient is an important parameter for a variety of reasons. For example, by determining the diffusion coefficient of various polymer and analyte combinations, it is possible to design a very efficient sensor system. Thus, the design and efficiency of polymer based sensors depend in part on the diffusion coefficient. Moreover, the optimum number and kind of polymers in the sensor array depends in part on the diffusion coefficient. Thus, if the analyte is an aromatic polar analyte, certain polymers are better than others. Using the methods of the present invention, optimum polymers can be determined because the polymer/analyte pair can be better matched.

In certain embodiments, an array of sensors comprise the same polymer, only the predetermined thickness of the polymer is different. In this aspect, the thinnest polymer sensor has the most resistance (i.e., fewer conductive paths to traverse) and the thickest polymer sensor shows the least resistance (i.e., the most conductive paths to traverse). However, the thinnest sensor will show steady-state conditions faster compared to the thickest sensor which reach steady state conditions at a slower pace. Accordingly, where a thickness of a sensor is known one can obtain merely obtain data at two instances very close in time. For example, with reference to FIG. 7, obtaining data at t=0 and t=0.5 seconds one would be able to determine the diffusion coefficient based upon the response of hexane on a "thin" or "thick" film sensor. In this way the thinner films will come to equilibrium and produce the equilibrium response data even at the short observation times whereas the thicker films will require longer times to come to equilibrium and at early time points will reflect the kinetic response of the sensor to the analyte. Thus through the use of a combination of thicknesses, one can obtain equilibrium and kinetic response data without having to record for a lengthy time period on one thick sensor and wait to equilibrium.

It is important to note that the thickness of the second material of the sensor does not need to be predetermined. It is helpful, although not essential, to have a predetermined thickness in providing for ease of calculating a diffusion coefficient. The thickness may be calculated subsequent to obtaining data from the interaction of the analyte or molecule with at least one sensor, as described herein. Furthermore, it is not essential that the polymer thickness be know for purposes of obtaining a "fingerprint" or "resistance profile" of an analyte. An unknown analyte profile or fingerprint can be compared to a desired profile or fingerprint to determine whether the unknown analyte has similar chemical or biological activity.

Sensor Applications

The sensors and sensor arrays disclosed herein act as an "electronic nose" to offer ease of use, speed, and identification of analytes and/or analyte regions all in a portable, relatively inexpensive implementation. Thus, a wide variety of analytes and fluids may be analyzed by the disclosed sensors, arrays and noses so long as the subject analyte is capable generating a detectable response across a plurality of sensors of the array. Analyte applications include broad ranges of chemical classes such as organics including, for example, alkanes, alkenes, alkynes, dienes, alicyclic hydrocarbons, arenes, alcohols, ethers, ketones, aldehydes, carbonyls, carbanions, biogenic amines, thiols, polynuclear aromatics and derivatives of such organics, e.g., halide derivatives, etc., biomolecules such as sugars, isoprenes and isoprenoids, fatty acids and derivatives, etc. Accordingly, commercial applications of the sensors, arrays and noses include environmental toxicology and remediation, biomedicine, materials quality control, food and agricultural products monitoring, anaesthetic detection, automobile oil or radiator fluid monitoring, breath alcohol analyzers, hazardous spill identification, explosives detection, fugitive emission identification, medical diagnostics, fish freshness, detection and classification of bacteria and microorganisms both in vitro and in vivo for biomedical uses and medical diagnostic uses, and the like. A wide variety of commercial applications are available for the sensors arrays and electronic noses including, but not limited to, environmental toxicology and remediation, biomedicine, materials quality control, food and agricultural products monitoring, heavy industrial manufacturing, ambient air monitoring, worker protection, emissions control, product quality testing, leak detection and identification, oil/gas petrochemical applications, combustible gas detection, $H_2S$ monitoring, hazardous leak detection and identification, emergency response and law enforcement applications, illegal substance detection and identification, arson investigation, enclosed space surveying, utility and power applications, emissions monitoring, transformer fault detection, food/beverage/agriculture applications, freshness detection, fruit ripening control, fermentation process monitoring and control applications, flavor composition and identification, product quality and identification, refrigerant and fumigant detection, cosmetic/perfume/fragrance formulation, product quality testing, personal identification, chemical/plastics/pharmaceutical applications, leak detection, solvent recovery effectiveness, perimeter monitoring, product quality testing, hazardous waste site applications, fugitive emission detection and identification, leak detection and identification, perimeter monitoring, transportation, hazardous spill monitoring, refueling operations, shipping container inspection, diesel/gasoline/aviation fuel identification, building/residential natural gas detection, formaldehyde detection, smoke detection, fire detection, automatic ventilation control applications (cooking, smoking, etc.), air intake monitoring, hospital/medical anesthesia & sterilization gas detection, infectious disease detection and breath applications, body fluids analysis, pharmaceutical applications, drug discovery and telesurgery. Another application for the sensor-based fluid detection device in engine fluids is an oil/antifreeze monitor, engine diagnostics for air/fuel optimization, diesel fuel quality, volatile organic carbon measurement (VOC), fugitive gases in refineries, food quality, halitosis, soil and water contaminants, air quality monitoring, leak detection, fire safety, chemical weapons identification, use by hazardous material teams, explosive detection, breathalyzers, ethylene oxide detectors and anesthetics.

Biogenic amines such as putrescine, cadaverine, and spermine are formed and degraded as a result of normal metabolic activity in plants, animals and microorganisms, and have been identified and quantified using analytical techniques such as gas chromatography-mass spectrometry (GC-MS), high performance liquid chromatography (HPLC) or array based vapor sensing in order to assess the freshness of foodstuffs such as meats (Veciananogues, 1997, *J. Agr. Food Chem.*, 45:2036–2041), cheeses, alcoholic beverages, and other fermented foods. Additionally, aniline and o-toluidine have been reported to be biomarkers for patients having lung cancer (Preti et al., 1988, *J. Chromat. Biomed. Appl.* 432:1–11), while dimethylamine and trimethylamine have been reported to be the cause of the "fishy" uremic breath odor experienced by patients with renal failure.(Simenhoff, 1977, *New England J. Med.*, 297:132–135) Thus, in general biogenic amines and thiols are biomarkers of bacteria, disease states, food freshness, and other odor-based conditions. Thus, the electronic nose sensors and arrays discussed herein incorporating these materials can be used to monitor the components in the headspace of urine, blood, sweat, and saliva of human patients, as well as breath, to diagnose various states of health and disease. In addition, they can be used for food quality monitoring, such as fish freshness (which involves volatile amine signatures), for environmental and industrial applications (oil quality, water quality, air quality and contamination and leak detection), for other biomedical applications, for law enforcement applications (breathalayzers), for confined space monitoring (indoor air quality, filter breakthrough, etc) and for other applications delineated above to add functionality and performance in an unanticipated fashion to existing sensor arrays though improvement in their properties by use in arrays that combine sensor modalities. For example, surface acoustic wave (SAW) arrays, quartz crystal microbalance arrays, composites consisting of regions of conductors and regions of insulators, bulk semi-conducting organic polymers, and other array types exhibit improved performance towards vapor discrimination and quantification when the sensors of the present invention are incorporated additionally into arrays that contain these other sensing modalities (e.g., wherein the array of sensors comprises a member selected from the group consisting of a metal oxide gas sensor, a conducting polymer sensor, a dye-impregnated polymer film on fiber optic detector, a polymer-coated micromirror, an electrochemical gas detector, a chemically sensitive field-effect transistor, a carbon black-polymer composite, a micro-electro-mechanical system device and a micro-opto-electro-mechanical system device).

Breath testing has long been recognized as a nonintrusive medical technique that might allow for the diagnosis of disease by linking specific volatile organic vapor metabolites in exhaled breath to medical conditions (see Table 1). Table 1 lists some of the volatile organic compounds that have been identified as targets for specific diseases using gas chromatography/mass spectrometry (GC/MS) methods, with emphasis on amines.

TABLE 1

| Patient Diagnosis | Target VOCs | VOC Source |
|---|---|---|
| Uremia; Preti, 1992; Simenhoff, 1977; Davies, 1997 | dimethylamine, trimethylamine | breath, urine |
| Trimethylaminuria; Preti. 1992: Alwaiz. | trimethylamine | breath, urine, swat, vaginal discharge |
| Preti, 1992; Alwaiz, 1989 | | vaginal discharge |
| Lung Cancer; Preti, 1992 | aniline, o-toluidine | lung air |
| Dysgeusia/Dysosmia; Preti, 1992; Oneill, 1988 | hydrogen sulfide, methyl mercaptn, pyridine, aniline, diphenylamine, dodecanol | lung air |
| Cystinuria; Manolis A., 1983, Clin. Chem. 29:5. | cadaverie, piperidine, putrescine, pyrrolidine | breath |
| Halitosis; Kozlovsky, 1994; Preti, 1992 | hydrogen sulfide, methyl mercaptan, cadaverine, putrescine, indole, skatole | mouth air |
| Bacterial Vaginosis; Chandiok, 1997, J. Clinical Path., 50:790. | amines | vaginal cavity and discharge |

With reference now to the drawings, and particularly to FIG. 1, there is shown a sensor array for detecting an analyte in a fluid for use in conjunction with an electrical measuring apparatus. The array comprises a plurality of sensors, at least one of the sensors comprising at least first and second conductive leads electrically coupled to and separated by regions of an a first conductive material and a second material compositionally different than the first conductive material, wherein the sensor provides an electrical path through the regions of the second material and the regions of the conductive material, wherein the sensor comprises at least one region of second material having a different thickness than at least one other region of second material, the second material being selected from the group consisting of conductive organic material, semi-conductive material and non-conductive or insulating material. The leads may be any convenient conductive material, usually a metal, and may be interdigitized to maximize signal-to-noise strength.

A sensor in the array is composed of a material comprising regions of an first conductive material with regions of a second compositionally dissimilar material. The sensor comprises a plurality of alternating regions of differing compositions and therefore differing conductivity transverse to the electrical path between the conductive leads. Generally, at least one of the sensors is fabricated by blending a conductive material with an a material compositionally different than the conductive material. For example, in a colloid, suspension or dispersion of particulate conductive material in a region of a second material that is compositionally different, the regions separating the particles provide changes in conductance relative to the conductance of the particles themselves. The gaps of different conductance arising from the dissimilar second material range in path length from about 10 to 1,000 angstroms, usually on the order of 100 angstroms. The path length and resistance of a given gap is not constant but rather is believed to change as the material absorbs, adsorbs or imbibes an analyte. Accordingly, the dynamic aggregate resistance provided by these gaps in a given resistor is a function of analyte permeation of the organic regions of the material. In some embodiments, the conductive material may also contribute to the dynamic aggregate resistance as a function of analyte permeation (e.g., when the conductive material is a conductive organic polymer such as polypyrrole and is blended with another organic conducting material to form the composite).

A wide variety of conductive materials and dissimilar second materials can be used. In one embodiment, one such combination is comprised of an inorganic (Au, Ag) or organic (carbon black) conductive material, while the other region is comprised of a compositionally dissimilar second material such as a polymer material (e.g., polyaniline, polypyrrole, polythiophene, polyEDOT, and other conducting organic polymers such as those in the Handbook of Conducting Polymers (Handbook of Conducting Polymers, second ed., Marcel Dekker, New York 1997, vols. 1 & 2)). Other combinations of conductor/dissimilar second material/composite materials are also useful.

Polyaniline is a desirable member in the class of conducting organic polymer materials in that the half oxidized form, the emeraldine base, is rendered electrically conductive upon incorporation of a strong acid. The conductive form of polyaniline, commonly referred to as the emeraldine salt (ES), has been reported to deprotonate to the emeraldine base and become insulating in alkaline environments. Without being bound to any particular theory, the polyaniline may also undergo a beneficial phase transition that also contributes to the superior performance of such composites.

Table 2 provides exemplary conductive materials for use in sensor fabrication; blends, such as of those listed, may also be used. Typically conductors include, for example, those having a positive temperature coefficient of resistance. The sensors are comprised of a plurality of alternating regions of a conductor with regions of a compositionally dissimilar material. Without being bound to any particular theory, it is believed that an electrical charge traverses between the two contacting electrodes traverses both the regions of the conductor and the regions of the second dissimilar material.

TABLE 2

| Major Class | Examples |
| --- | --- |
| Organic Conductors | conducting polymers (poly(anilines), poly(thiophenes), poly(pyrroles), poly(aceylenes, etc.)), carbonaceous material (carbon blacks, graphite, coke, C60 etc.), charge transfer complexes (tetramethylparaphenylenediamine-chloranile, alkali metal tetracyanoquinodimethane complexes, tetrathiofulvalene halide complexes, etc.), etc. |
| Inorganic Conductors | metals and metal alloys (Ag, Au, Cu, Pt, AuCu alloy, etc.), highly doped semiconductors (Si, GaAs, InP, MoS2, TiO2, etc.), conductive metal oxides (In2O3, SnO2, Na2Pt3O4, etc.), superconductors (Yba2Cu3O7, Ti2Ba2Ca2Cu3O10, etc.), etc. |
| Mixed inorganic/organic Conductor | Tetracyanoplatinate complexes, Iridium halocarbonyl complexes, stacked macrocyclic complexes. Etc. |

In this embodiment, the conducting region can be anything that can carry electrons from atom to atom, including, but not limited to, a material, a particle, a metal, a polymer, a substrate, an ion, an alloy, an organic material, (e.g., carbon, graphite, etc.) an inorganic material, a biomaterial, a solid, a liquid, a gas or regions thereof.

In certain other embodiments, the conductive material is a conductive particle, such as a colloidal nanoparticle. As used herein the term "nanoparticle" refers to a conductive cluster, such as a metal cluster, having a diameter on the nanometer scale. Such nanoparticles are optionally stabilized with organic ligands.

Examples of colloidal nanoparticles for use in accordance with the present invention are described in the literature. In this embodiment, the organic region can optionally be a ligand that is attached to a central core making up the nanoparticle. These ligands i.e., caps, can be polyhomo- or polyhetero-functionalized, thereby being suitable for detecting a variety of chemical analytes. The nanoparticles, i.e., clusters, are stabilized by the attached ligands. In certain embodiments, the conducting component of the resistors are nanoparticles comprising a central core conducting element and an attached ligand optionally in a polymer matrix. With reference to Table 2, various conducting materials are suitable for the central core. In certain embodiments, the nanoparticles have a metal core. Typcial metal cores include, but are not limited to, Au, Ag, Pt, Pd, Cu, Ni, AuCu and regions thereof. Gold (Au) is especially preferred. These metallic nanoparticles can be synthesized using a variety of methods. In a preferred method of synthesis, a modification of the protocol developed by Brust et al. can be used. (see, Brust, M.; Walker, M.; Bethell, D.; Schiffrin, D. J.; Whyman, R. *J. Chem. Soc., Chem. Commun.,* 1994, 801–802.) As explained more fully below, by varying the concentration of the synthetic reagents, the particle size can be manipulated and controlled.

Table 3 provides exemplary conductive organic materials that can be used to form a the second dissimilar material regions of the sensors.

TABLE 3 a 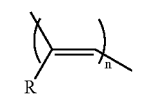

R = alkyl, alkoxy b 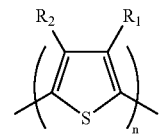

R1 = H, alkyl, alkoxy
R2 = H, alkyl, alkoxy c 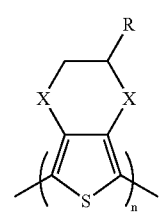

X = S, O
R = H, alkyl, alkoxy

TABLE 3-continued d.

X1 = S, O, N–H, N–R
X2 = C, N
X3 = C, N
R1 = H, alkyl, alkoxy
R2 = H, alkyl, alkoxy e.

R1 = H, alkyl
R2 = H, alkyl, alkoxy
R3 = H, alkyl, alkoxy f.

R1 = H, alkyl
R2 = H, alkyl, alkoxy g.

R1 = H, alkyl, propanesulfonate
R2 = H, alkyl, alkoxy, sulfonate h.

R1 = H, alkyl, alkoxy
R2 = H, alkyl, alkoxy i.

R1 = H, alkyl, alkoxy
R2 = H, alkyl, alkoxy j.

X = S, O, N–H, N–R k.

X = S, O, N–H, N–R
R = alkyl l.

X1 = S, O, N–H, N–R
X2 = S, O, N–H, N–R
R1 = H, alkyl, alkoxy
R2 = H, alkyl, alkoxy
R3 = H, alkyl, alkoxy
R4 = H, alkyl, alkoxy
R = alkyl m.

X1 = S, O, N–H, N–R
X2 = S, O, N–H, N–R n.

X1 = S, O, N–H, N–R
X2 = S, O, N–H, N–R
X3 = S, O, N–H, N–R
R = alkyl
R1 = H, alkyl, alkoxy
R2 = H, alkyl, alkoxy
R3 = H, alkyl, alkoxy
R4 = H, alkyl, alkoxy
R5 = H, alkyl, alkoxy
R6 = H, alkyl, alkoxy o.

X = S, O, N–H, N–R
R = alkyl

TABLE 3-continued p 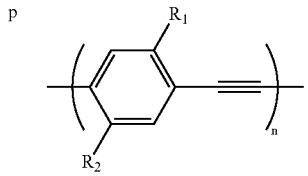

R1 = H, alkyl, alkoxy
R2 = H, alkyl, alkoxy q 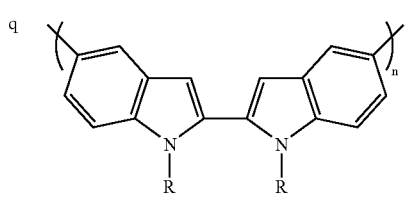

R1 = H, alkyl r 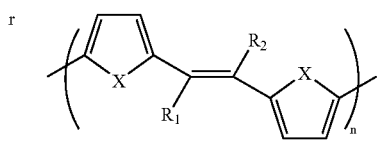

X = S, O, N–H, N–R
R1 = H, alkyl, alkoxy
R2 = H, alkyl, alkoxy s 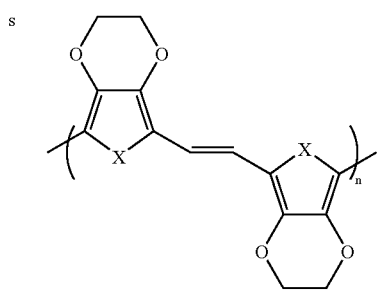

X = S, O, N–H, N–R t 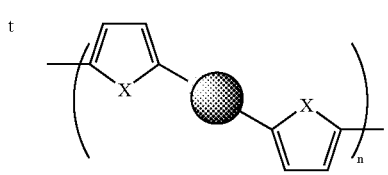

X = S, O, N–H, N–R
 = aromatic ring system

TABLE 3-continued u 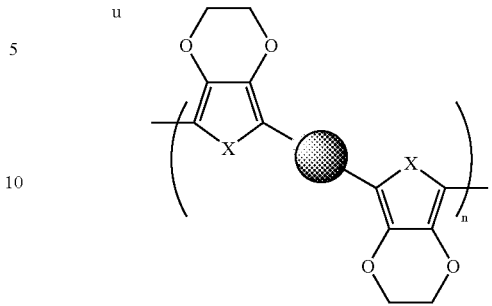

X = S, O, N–H, N–R
 = aromatic ring system v 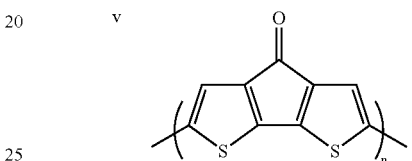

w 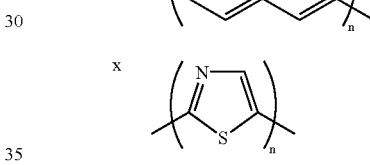

x 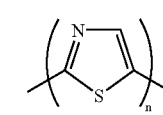

y 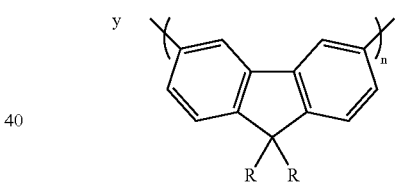

R = H, alkyl, alkoxy z 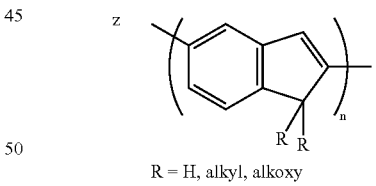

R = H, alkyl, alkoxy a. Poly(acetylene) and derivative
b. Poly(thiophenes) and derivatives
c. Poly(3,4-ethylenedioxythiophene) and poly(3,4-ethylenedithiathiophene) and derivatives
d. Poly(isathianaphthene), poly(pyridothiophene), poly(pyrizinothiophene), and derivatives
e. Poly(pyrrole) and derivatives
f. Poly(3,4-ethylenedioxypyrrole) and derivatives
g. Poly(aniline) and derivatives
h. Poly(phenylenevinylene) and derivatives
I. Poly(p-phenylene) and derivatives
j. Poly(thianapthene), poly(benxofuran), and poly(indole) and derivatives
k. Poly(dibenzothiophene), poly(dibenxofuran), and poly(carbazole) and derivatives
l. Poly(bithiophene), poly(bifuran), poly(bipyrrole), and derivatives
m. Poly(thienothiophene), poly(thienofuran), poly(thienopyrrole), poly (furanylpyrrole), poly(furanylfuran), poly(pyrolylpyrrole), and derivatives
n. Poly(terthiophene), poly(terfuran), poly(terpyrrole), and derivatives

TABLE 3-continued o. Poly(dithienothiophene), poly(difuranylthiophene), poly(dipyrrolylthiophene), poly(dithienofuran), poly(dipyrrolylfuran), poly(dipyrrolylpyrrole) and derivatives
p. Poly(phenyl acetylene) and derivatives
q. Poly(biindole) and derivatives
r. Poly(dithienovinylene), poly(difuranylvinylene), poly(dipyrrolylvinylene) and derivatives
s. Poly(1,2-trans(3,4-ethylenedioxythienyl)vinylene), poly(1,2-trans(3,4-ethylenedioxyfuranyl)vinylene), and poly(1,2-trans(3,4-ethylenedioxypyrrolyl)vinylene), and derivatives
t. The class of poly(bis-thienylarylenes) and poly(bis-pyrrolylarylenes) and derivatives
u. The class of poly(bis(3,4-ethylenedioxythienyl)arylenes) and derivatives
v. Poly (dithienylcyclopentenone)
w. Poly(quinoline)
x. Poly(thiazole)
y. Poly(fluorene) and derivatives
z. Poly(azulene) and derivatives
Notes:
a. Aromatics = phenyl, biphenyl, terphenyl, carbazole, furan, thiophene, pyrrole, fluorene, thiazole, pyridine, 2,3,5,6-hexafluorobenzene, anthracene, coronene, indole, biindole, 3,4-ethylenedioxythiophene, 3,4-ethylenedioxypyrrole, and both the alkyl and alkoxy derivatives of these aromatics.
b. Alkyl = aliphatic group branched or straight chain ranging from $CH_3$ to $C_{20}H_{41}$.
c. Alkoxy = OR, where R is an aliphatic group that may either be branched or straight chain ranging from $CH_3$ to $C_{20}H_{41}$.
d. All conductive polymers are depicted in their neutral, nonconductive form. The polymers listed in the FIGURE are doped oxidatively either by means chemically or electrochemically.
e. The class of polyanilines are acid doped and can be done so with a number of sulfonic acids including methane sulfonic acid, ethane sulfonic acid, propane sulfonic acid, butane sulfonic acid, pentane sulfonic acid, hexane sulfonic acid, heptane sulfonic acid, octane sulfonic acid, nonane sulfonic acid, decane sulfonic acid, ondecane sulfonic acid, dodecane sulfonic acid, dodecylbenzenesulfonic acid, toluene sulfonic acid, benzene sulfonic acid, dinonanylnaphthalene sulfonic acid, and both the d and l forms of camphor sulfonic acid.
f. All other class of conductive polymers when doped there is an associated counter ion to compensate the positive charges on the backbone. These can be perchlorate, hexafluorophosphate, tetrafluoroborate, fluoride, chloride, bromide, iodide, triflate, etc.

The organic material can be either an organic semiconductor or organic conductor. "Semi-conductors" as used herein, include materials whose electrical conductivity increases as the temperature increases, whereas conductors are materials whose electrical conductivity decreases as the temperature increases. By this fundamental definition, the organic materials that are useful in the sensors of the present invention are either semiconductors or conductors. Such materials are collectively referred to herein as organic materials because they produce a readily-measured resistance between two conducting leads separated by about 10 micron or more using readily-purchased multimeters having resistance measurement limits of 100 Mohm or less, and thus allow the passage of electrical current through them when used as elements in an electronic circuit at room temperature. Semi-conductors and conductors can be differentiated from insulators by their different room temperature electrical conductivity values. Insulator show very low room temperature conductivity values, typically less than about $10^{-8}$ ohm$^{-1}$ cm$^{-1}$. Poly(styrene), poly(ethylene), and other polymers elaborated in Table 4 provide examples of insulating or "non-conductive" materials. Metals have very high room temperature conductivities, typically greater than about 10 ohm$^{-1}$ cm$^{-1}$. Semi-conductors have conductivities greater than those of insulators, and are distinguished from metals by their different temperature dependence of conductivity, as described above. Examples of semi-conducting and conducting organic material are provided in Table 3. The organic materials that are useful in the sensors of the present invention are either semiconductors or conductors, and have room temperature electrical conductivities of greater than about $10^{-6}$ ohm$^{-1}$ cm$^{-1}$, preferably having a conductivity of greater than about 10–3 ohm$^{-1}$ cm$^{-1}$.

Accordingly, the sensors of the present invention include sensors comprising regions of an electrical conductor and regions of a compositionally different material that is an electrical conductor, semiconductor, or non-conductive material. As used above, electrical conductors include, for example, Au, Ag, Pt and carbon black, other conductive materials having similar resistivity profiles are easily identified in the art (see, for example the latest edition of: *The CRC Handbook of Chemistry and Physics*, CRC Press, the disclosure of which is incorporated herein by reference). Furthermore, non-conductive materials (i.e., insulators) can also be incorporated into the composite to further manipulate the analyte response properties of the composites. The insulating region (i.e., non-conductive region) can be anything that can impede electron flow from atom to atom, including, but not limited to, a polymer, a plasticizer, an organic material, an organic polymer, a filler, a ligand, an inorganic material, a biomaterial, a solid, a liquid, a gas and combinations thereof. Table 4 provides examples of a non-conductive second material (i.e., a second material that is compositionally different than the conductive material of a sensor) that can be used for such purposes.

TABLE 4

| Major Class | Examples |
| --- | --- |
| Main-chain carbon polymers | poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitrites), poly(vinyl esters), poly(styrenes), poly(aryines), etc. |
| Main-chain acyclic heteroatom polymers | poly(oxides), poly(caronates), poly(esters), poly(anhydrides), poly(urethanes), poly(sulfonate), poly(siloxanes), poly(sulfides), poly(thioesters), poly(sulfones), poly(sulfonamindes), poly(amides), poly(ureas), poly(phosphazens), poly(silanes), poly(silazanes), etc. |
| Main-chain heterocyclic polymers | poly(furantetracarboxylic acid diimides), poly(benzoxazoles), poly(oxadiazoles), poly(benzothiazinophenothiazines), poly(benzothiazoles), poly(pyrazinoquinoxalines), poly(pyromenitimides), poly(quinoxalines), poly(benzimidazoles), poly(oxidoles), poly(oxoisinodolines), poly(diaxoisoindoines), poly(triazines), poly(pyridzaines), poly(pioeraziness), poly(pyridinees), poly(pioeridiens), poly(triazoles), poly(pyrazoles), poly(pyrrolidines), poly(carboranes), poly(oxabicyclononanes), poly(diabenzofurans), poly(phthalides), poly(acetals), poly(anhydrides), carbohydrates, etc. |

Nonconductive organic polymer materials; blends and copolymers; plasticized polymers; and other variations including those using the polymers listed here, may also be used. Combinations, concentrations, blend stoichiometries, percolation thresholds, etc. are readily determined empirically by fabricating and screening prototype resistors (chemiresistors) as described below.

Sensor Fabrication

The sensors of the invention can be fabricated by many techniques such as, but not limited to, solution casting, suspension casting, air-brush techniques and mechanical mixing.

The sensors as described above can be fabricated by using a standard painter's air-brush (or equivalents easily recognized in the art). For example, an air-brush can be used to coat a substrate with a mixture of any number of various combinations of the foregoing conductive materials and a second material that is compositionally different than the conductive material.

In one embodiment, a polymer solution or suspension is placed in a reservoir and the reservoir attached to a compressed gas system. The flowing gas sucks up the solution or suspension by a vacuum created in the air brush system, which is then ejected from a nozzle of the air brush. This flow of solution or suspension (e.g., polymer, solvent and suspended material) is directed toward a substrate that has been prepared to receive the polymer solution or suspension. The polymer solution or suspension can be stirred either continuously or intermittently while in the reservoir in order to maintain a homogenous mixture.

The method of the invention is amenable to automation using, for example, a computer system to control the rate and amount of polymer solution or suspension ejected from a nozzle of the air brush system. Accordingly, it will be recognized that the method of the invention is capable of fabricating many sensors in the time it would take to make one using the standard methods of dip coating or spin coating. Additionally, the method of the invention is capable of high reproducibility in sensor fabrication.

It will also be recognized that the method of the invention makes it possible to simply and efficiently fabricate sensors from various and odd shaped substrates. For example, the substrates need not be flat as required by standard spin coating techniques.

The substrates can be prepared such that a large number of substrates are contacted by a single pass of the air-brush system. This leads to a large number of very reproducible sensors (determined by baseline resistance) in a simple and time efficient process.

In addition, the method of the invention lends itself to making simple changes in sensor thickness and sensor compositions. For example, if a sensor is desired that has a thicker polymer coating than another sensor, the system merely ejects more polymer solution or suspension or ejects for a longer period of time at a particular location in an array of sensors or on a particular sensor.

In addition, the methods of the invention could be used to fabricate sensors having small wells or specific regions on an otherwise smooth surface. The method involves ejecting a solution or suspension of polymer as a fine jet or stream directed to a particular location on a substrate or sensor. In other words, the spray jet could be made to pass over the whole substrate (as described above) or directed at only a small area thus containing the coated region without the need for mask to prevent coating or non-desired regions. Accordingly, depending on the type of application required custom nozzles that provide custom jets or streams of polymer could be designed. For example, nozzles that provide conical sprays, linear sprays, planer sprays, or other spray geometries can be designed to those of skill in the art. A number of substrates may be employed for this purpose including, but not limited to, those formed of metals, organic polymers, inorganic polymers, ceramics, textiles, and composites thereof.

For systems where the conducting and/or the compositionally dissimilar material or their reaction precursors are soluble in a common solvent, the sensor (e.g., the chemiresistor) can be fabricated by solution casting. The oxidation of pyrrole by phosphomolybdic acid represents such a system. In this reaction, the phosphomolybdic acid and pyrrole are dissolved in tetrahydrofuran (THF) and polymerization occurs upon solvent evaporation. For example, this method allows for THF soluble compositionally different conductive, semiconductive, and non-conductive materials to be dissolved into this reaction region thereby allowing the composite to be formed in a single step upon solvent evaporation.

Certain conducting organic polymers can also be synthesized via a soluble precursor polymer. In these cases, blends between the precursor polymer and the compositionally different material of the composite can first be formed followed by chemical reaction to convert the precursor polymer into the desired conducting polymer. For instance poly(p-phenylene vinylene) can be synthesized through a soluble sulfonium precursor. Blends between this sulfonium precursor and a non-conductive or conductive polymer can be formed by solution casting. After which, the blend can be subjected to thermal treatment under vacuum to convert the sulfonium precursor to the desired poly(p-phenylene vinylene).

In suspension casting, one or more of the components of the sensor is suspended and the others dissolved in a common solvent. Suspension casting is a rather general technique applicable to a wide range of species, such as carbon blacks or colloidal metals, which can be suspended in solvents by vigorous mixing or sonication. In one application of suspension casting, the organic or conductive polymer is dissolved in an appropriate solvent (such as THF, acetonitrile, water, etc.). Carbon black is then suspended in this solution and the resulting region is used to dip coat or spray coat electrodes.

Mechanical mixing is suitable for all of the conductive/ conductive organic/non-conductive combinations possible. In this technique, the materials are physically mixed in a ball-mill or other mixing device. For instance, carbon black/ conducting organic polymer composites are readily made by ball-milling. When the semi-conductive or conductive organic material can be melted or significantly softened without decomposition, mechanical mixing at elevated temperature can improve the mixing process. Alternatively, composite fabrication can sometimes be improved by several sequential heat and mix steps.

Once fabricated, the individual sensors can be optimized for a particular application by varying their chemical make up and morphologies. The chemical nature of the sensors determines to which analytes they will respond and their ability to distinguish different analytes. The relative ratio of conductive to compositionally different material (e.g., non-conductive, semi-conductive material), along with the composition of any other insulating organic or inorganic components, can determine the magnitude of the response since the resistance of the elements becomes more sensitive to sorbed molecules as the percolation threshold is approached and as the molecules interact chemically with the components of the composite that adsorb or absorb the analyte. The film morphology is also important in determining response characteristics. For instance, uniform thin films respond more quickly to analytes than do uniform thick ones. Hence, with an empirical catalogue of information on chemically diverse sensors made with varying ratios of semiconductive, conducting, and insulating components and by differing fabrication routes, sensors can be chosen that are appropriate for the analytes expected in a particular application, their concentrations, and the desired response times. Further optimization can then be performed in an iterative fashion as feedback on the performance of an array under particular conditions becomes available. As mentioned above, by varying the thickness of, for example, the organic material of the sensor it is possible to obtain information regarding the diffusion characteristics of a certain analyte or molecule of interest.

Sensor arrays particularly well-suited to scaled up production are fabricated using integrated circuit (IC) design technologies. For example, the sensor can easily be integrated onto the front end of a simple amplifier interfaced to an A/D converter to efficiently feed the data stream directly into a neural network software or hardware analysis section. Micro-fabrication techniques can integrate the sensor directly onto a micro-chip which contains the circuitry for analog signal conditioning/processing and then data analysis. This provides for the production of millions of incrementally different sensor elements in a single manufacturing step using, for example, ink-jet technology.

In one embodiment, the sensor arrays have a predetermined inter-sensor variation in the structure, thickness or composition of the first conductive material or the second compositionally different materials as well as in the conductive components and any insulating or plasticizing components of the composites. The variation may be quantitative and/or qualitative. For example, the concentration of the conductive or semi-conductive organic material in the composite can be varied across sensors. Alternatively, a variety of different organic materials may be used in different sensors. This ability to fabricate many chemically different materials allows ready incorporation of a wide range of chemical diversity into the sensor elements, and also allows facile control over the electrical properties of the sensor elements through control over the composition of an individual sensor element in the array. Insulating organic materials can also be used and blended into the array in order to further increase the diversity in one embodiment of the invention. Commercially available, off-the-shelf, organic polymers can provide the basic sensor components that respond differently to different analytes, based on the differences in polarity, molecular size, and other properties of the analyte in order to achieve the chemical diversity amongst array elements in the electronic nose sensors. Such diversity can be further enhanced by varying the thickness of a sensor or region of a sensor. Otherwise, these properties can be obtained by modification in the composition of the electrically conductive or reactive second material component of the sensor composition by use of capping agents on a colloidal metal part of the conductive phase, by use of different plasticizers added to otherwise compositionally identical sensor elements to manipulate their analyte sorption and response properties, by variation in the temperature or measurement frequency of the sensors in an array of sensors that are otherwise compositionally identical, or a combination thereof and with sensors that are compositionally different as well. The sensors in an array can readily be made by combinatorial methods in which a limited number of feedstocks are combined to produce a large number of chemically distinct sensor elements.

As used herein the term "predetermined" means that the conductive film layer associated with the sensor has, for example, a predefined or predetermined thickness which is measured within about 1 nm using atomic force microscopy, scanning tunneling microscopy, profilometry or other suitable method known by those of skill in the art.

One method of enhancing the diversity of polymer based conductor/conductor, conductor/semiconductor conductor/insulator, sensors and combinations thereof is through the use of polymer blends or copolymers (Doleman, et al. (1998) *Anal. Chem.* 70, 2560–2654). Immiscible polymer blends may also be of interest because carbon black or other conductors can be observed to preferentially segregate into one of the blend components.

Sensor arrays allow expanded utility because the signal for an imperfect "key" in one channel can be recognized through information gathered on another, chemically or physically dissimilar channel in the array. A distinct pattern of responses produced over the collection of sensors in the array can provide a fingerprint that allows classification and identification of the analyte, whereas such information would not have been obtainable by relying on the signals arising solely from a single sensor or sensing material. In addition, by varying the thickness of regions or whole sensors a distinctive pattern may be further expanded to include data on the diffusion coefficient of a particular molecule or analyte. The data may be obtained through the measurement of a single sensor, which measures the diffusion through a certain organic material (e.g., a semi-conductive or non-conductive material) or through the diffusion of a number of dissimilar materials.

The general method for using the disclosed sensors, arrays and electronic noses, for detecting the presence of an analyte in a fluid, where the fluid is a liquid or a gas, involves resistively sensing the presence of an analyte in a fluid with a chemical sensor comprising first and second conductive leads electrically coupled to and separated by a chemically sensitive sensor as described above by measuring a first resistance between the conductive leads when the resistor is contacted with a first fluid comprising first analyte and a second, different resistance when the resistor is contacted with a second, different fluid. Where a diffusion coefficient is to be determined a resistivity at a first time when contacted with the analyte is measured followed by a measurement of resistivity at a second time. If the measurements are by analog signal the measurements may be obtained continuously during the time period for measuring the diffusion of the analyte. Where an analog to digital converter is present measurements that are essentially continuous can be obtained.

An ideal detector array would produce a unique signature for every different analyte to which it was exposed. To construct such a system, it is necessary to include detectors that probe important, but possibly subtle, molecular parameters such as, for example chirality. The term "chiral" is used herein to refer to an optically active or enantiomerically pure compound, or to a compound containing one or more asymmetric centers in a well-defined optically active configuration. A chiral compound is not superimposable upon its mirror image. Harnessing enantiomer resolution gives rise to myriad applications. For instance, because the active sites of enzymes are chiral, only the correct enantiomer is recognized as a substrate. Thus, pharmaceuticals having near enantiomeric purity are often many more times active than their racemic mixtures. However, many pharmaceutical formulations marketed today are racemic regions of the desired compound and its "mirror image." One optical form (or enantiomer) of a racemic region may be medicinally useful, while the other optical form may be inert or even harmful, as has been reported to be the case for thalidomide.

In this fashion, the sensors and sensor arrays would be useful in assessing which form of chirality, and of what enantiomeric excess, was present in an analyte in a fluid. Due to the presence of chiral moieties, many biomolecules, such as amino acids, are amenable to detection using the sensor arrays of the present invention.

Similarly, by characterizing the diffusion characteristics of a molecule or analyte, it is possible to screen for molecules or analytes having diffusion coefficients similar or identical to a desired diffusion coefficient. This is useful in identifying molecules useful as pharmaceutical. For example, a beneficial drug or biological agent of interest may demonstrate a particular binding affinity for a polymer material of interest. This same biological agent may have better efficacy due to its diffusion through biological membranes. Accordingly, screening combinatorial drugs for biological agents using the sensors of the invention can measure not only the biological agent's binding affinity but its chirality and diffusion coefficient.

In another embodiment, the sensor for detecting the presence of a chemical analyte in a fluid comprises a sensor electrically coupled to an electrical measuring apparatus where the sensor is in thermal communication with a temperature control apparatus. As described above, the sensor comprises regions of a first conductive material and regions of a second material that is is compositionally different than the first conductive material. The sensor provides an electrical path through which electrical current may flow and a resistance (R) at a temperature (T) when contacted with a fluid comprising a chemical analyte.

In operation, the sensor(s) for detecting the presence of a chemical analyte in a fluid provide an electrical resistance ($R_m$) when contacted with a fluid comprising a chemical analyte at a particular temperature ($T_m$). The electrical resistance observed may vary as the temperature varies, thereby allowing one to define a unique profile of electrical resistances at various different temperatures for any chemical analyte of interest. In addition, the profile will include data characteristic of the diffusion coefficient of the analyte of interest. The diffusion coefficient will also be affected by the temperature as discussed above. For example, a chemically sensitive resistor, when contacted with a fluid comprising a chemical analyte of interest, will provide an electrical resistance $R_m$ at temperature $T_m$ where m is an integer greater than 1, and may provide a different electrical resistance $R_n$ at a different temperature $T_n$. The difference between $R_m$ and $R_n$ is readily detectable by an electrical measuring apparatus. If the sensor comprises an array of two or more sensors each being in thermal communication with a temperature control apparatus, one may vary the temperature across the entire array (i.e., generate a temperature gradient across the array), thereby allowing electrical resistances to be measured simultaneously at various different temperatures and for various different resistor compositions. For example, in an array of sensors, one may vary the composition of the sensors in the horizontal direction across the array, such that sensor composition in the vertical direction across the array remains constant. One may then create a temperature gradient in the vertical direction across the array, thereby allowing the simultaneous analysis of chemical analytes at different sensor compositions and different temperatures.

Methods for placing chemically sensitive resistors in thermal communication with a temperature control apparatus are readily apparent to those skilled in the art and include, for example, attaching a heating or cooling element to the sensor and passing electrical current through said heating or cooling element.

In yet another embodiment, rather than subjecting the sensor to a direct electrical current and measuring the true electrical resistance through the sensor(s) can be subjected to an alternating electrical current at different frequencies to measure impedance. Impedance is the apparent resistance in an alternating electrical current as compared to the true electrical resistance in a direct current. As such, the present invention is also directed to a sensor for detecting the presence of a chemical analyte in a fluid, said sensor connected to an electrical measuring apparatus, the sensor comprising regions of a first conductive material and a second material compositionally different than the first conductive material and wherein said sensor provides (a) an electrical path through said region of organic material and said conductive material, and (b) an electrical impedance $Z_m$ at frequency m when contacted with a fluid comprising an analyte, where m is an integer greater than 1 and m does not equal 0. One skilled in the art will recognize that variations in thickness of the sensor materials can be implemented to measure a diffusion coefficient. For measuring impedance as a function of frequency, the frequencies employed will generally range from about 1 Hz to 5 GHz, usually from about 1 MHZ to 1 GHz, more usually from about 1 MHZ to 10 MHZ and preferably from about 1 MHZ to 5 MHZ. An analyte will exhibit unique impedance characteristics at varying alternating current frequencies, thereby allowing one to detect the presence of any chemical analyte of interest in a fluid by measuring $Z_m$ at alternating frequency m. Similarly, the impedance will vary according to the diffusion of the analyte in the sensor.

For performing impedance measurements, one may employ virtually any impedance analyzer known in the art. For example, a Schlumberger Model 1260 Impedance/Gain-Phase Analyzer (Schlumberger Technologies, Farmborough, Hampshire, England) with approximately 6 inch RG174 coaxial cables is employed. In such an apparatus, the resistor/sensor is held in an A1 chassis box to shield it from external electronic noise.

In still another embodiment of the present invention, one may vary both the frequency m of the electrical current employed and the temperature $T_n$ and measure the electrical impedance $Z_{m,n}$, thereby allowing for the detection of the presence of a chemical analyte of interest.

An electronic nose for detecting an analyte in a fluid is fabricated by electrically coupling the sensor leads of an array of sensors to an electrical measuring device. The device measures changes in signal at each sensor of the array, preferably simultaneously and preferably over time. Preferably, the signal is an electrical resistance, although it could also be an impedance or other physical property of the material in response to the presence of the analyte in the fluid. Frequently, the device includes signal processing means and is used in conjunction with a computer and data structure for comparing a given response profile to a structure-response profile database for qualitative and quantitative analysis. Typically such a nose comprises usually at least ten, often at least 100, and perhaps at least 1000 different sensors though with mass deposition fabrication techniques described herein or otherwise known in the art, arrays of on the order of at least one million sensors are readily produced.

In one embodiment, the temporal response of each sensor (resistance as a function of time) is recorded. The temporal response of each sensor may be normalized to a maximum percent increase and percent decrease in signal which produces a response pattern associated with the exposure of the analyte. By iterative profiling of known analytes, a structure-function database correlating analytes and response profiles is generated. Unknown analytes may then be characterized or identified using response pattern comparison and recognition algorithms. Accordingly, analyte detection systems comprising sensor arrays, an electrical measuring device for detecting resistance across each chemiresistor, a computer, a data structure of sensor array response profiles, and a comparison algorithm are provided. In another embodiment, the electrical measuring device is an integrated circuit comprising neural network-based hardware and a digital-analog converter (DAC) multiplexed to each sensor, or a plurality of DACs, each connected to different sensor(s).

The desired signals if monitored as dc electrical resistances for the various sensor elements in an array can be read merely by imposing a constant current source through the resistors and then monitoring the voltage across each resistor through use of a commercial multiplexable 20 bit analog-to-digital converter. Such signals are readily stored in a computer that contains a resident algorithm for data analysis and archiving. Signals can also be preprocessed either in digital or analog form; the latter might adopt a resistive grid configuration, for example, to achieve local gain control. In addition, long time adaptation electronics can be added or the data can be processed digitally after it is collected from the sensors themselves. This processing could be on the same chip as the sensors but also could reside on a physically separate chip or computer.

Data analysis can be performed using standard chemometric methods such as principal component analysis and SIMCA, which are available in commercial software packages that run on a PC or which are easily transferred into a computer running a resident algorithm or onto a signal analysis chip either integrated onto, or working in conjunction with, the sensor measurement electronics. The Fisher linear discriminant is one preferred algorithm for analysis of the data, as described below. In addition, more sophisticated algorithms and supervised or unsupervised neural network based learning/training methods can be applied as well (Duda, R. O.; Hart, P. E. *Pattern Classification and Scene Analysis;* John Wiley & Sons: New York, 1973, pp 482).

The signals can also be useful in forming a digitally transmittable representation of an analyte in a fluid. Such signals could be transmitted over the Internet in encrypted or in publicly available form and analyzed by a central processing unit at a remote site, and/or archived for compilation of a data set that could be mined to determine, for example, changes with respect to historical mean "normal" values of the breathing air in confined spaces, of human breath profiles, and of a variety of other long term monitoring situations where detection of analytes in fluids is an important value-added component of the data.

20–30 different sensors is sufficient for many analyte classification tasks but larger array sizes can be implemented as well. Temperature and humidity can be controlled but because a preferred mode is to record changes relative to the ambient baseline condition, and because the patterns for a particular type and concentration of odorant are generally independent of such baseline conditions, it is not critical to actively control these variables in some implementations of the technology. Such control could be achieved either in open-loop or closed-loop configurations.

The sensors and sensor arrays disclosed herein could be used with or without preconcentration of the analyte depending on the power levels and other system constraints demanded by the user. Regardless of the sampling mode, the characteristic patterns (both from amplitude and temporal features, depending on the most robust classification algorithm for the purpose) associated with certain disease states and other volatile analyte signatures can be identified using the sensors disclosed herein. These patterns are then stored in a library, and matched against the signatures emanating from the sample to determine the likelihood of a particular odor falling into the category of concern (disease or non-disease, toxic or nontoxic chemical, good or bad polymer samples, fresh or old fish, fresh or contaminated air etc.).

Analyte sampling will occur differently in the various application scenarios. For some applications, direct headspace samples can be collected using either single breath and urine samples in the case of sampling a patient's breath for the purpose of disease or health state differentiation and classification. In addition, extended breath samples, passed over a Tenax, Carbopack, Poropak, Carbosieve, or other sorbent preconcentrator material, can be obtained when needed to obtain robust intensity signals. The absorbent material of the fluid concentrator can be, but is not limited to, a nanoporous material, a microporous material, a chemically reactive material, a nonporous material and combinations thereof. In certain instances, the absorbent material can concentrate the analyte by a factor that exceeds a factor of about $10^5$, or by a factor of about $10^2$ to about $10^4$. In another embodiment, removal of background water vapor is conducted in conjunction, such as concomitantly, with the concentration of the analyte. Once the analyte is concentrated, it can be desorbed using a variety of techniques, such as heating, purging, stripping, pressuring or a combination thereof.

Breath samples can be collected through a straw or suitable tube in a patient's mouth that is connected to the sample chamber (or preconcentrator chamber), with the analyte outlet available for capture to enable subsequent GC/MS or other selected laboratory analytical studies of the sample. In other applications, headspace samples of odorous specimens can be analyzed and/or carrier gases can be used to transmit the analyte of concern to the sensors to produce the desired response. In still other cases, the analyte will be in a liquid phase and the liquid phase will be directly exposed to the sensors; in other cases the analyte will undergo some separation initially and in yet other cases only the headspace of the analyte will be exposed to the sensors.

Using the device of the present invention, the analyte can be concentrated from an initial sample volume of about 10 liters and then desorbed into a concentrated volume of about 10 milliliters or less, before being presented to the sensor array.

Suitable commercially available adsorbent materials include but are not limited to, Tenax TA, Tenax GR, Carbotrap, Carbopack B and C, Carbotrap C, Carboxen, Carbosieve SIII, Porapak, Spherocarb, and combinations thereof. Preferred adsorbent combinations include, but are not limited to, Tenax GR and Carbopack B; Carbopack B and Carbosieve SIII; and Carbopack C and Carbopack B and Carbosieve SIII or Carboxen 1000. Those skilled in the art will know of other suitable absorbent materials.

In some cases, the array will not yield a distinct signature of each individual analyte in a region, unless one specific type of analyte dominates the chemical composition of a sample. Instead, a pattern that is a composite, with certain characteristic temporal features of the sensor responses that aid in formulating a unique relationship between the detected analyte contents and the resulting array response, will be obtained.

In a one embodiment of signal processing, the Fisher linear discriminant searches for the projection vector, w, in the detector space, which maximizes the pairwise resolution factor, i.e., rf, for each set of analytes, and reports the value of rf along this optimal linear discriminant vector. The rf value is an inherent property of the data set and does not depend on whether principal component space or original detector space is used to analyze the response data. This resolution factor is basically a multi-dimensional analogue to the separation factors used to quantify the resolving power of a column in gas chromatography, and thus the rf value serves as a quantitative indication of how distinct two patterns are from each other, considering both the signals and the distribution of responses upon exposure to the analytes that comprise the solvent pair of concern. For example, assuming a Gaussian distribution relative to the mean value of the data points that are obtained from the responses of the array to any given analyte, the probabilities of correctly identifying an analyte as a or b from a single presentation when a and b are separated with resolution factors of 1.0, 2.0 or 3.0 are approximately 76%, 92% and 98% respectively.

To compute the rf, from standard vector analysis, the mean response vector, $x_a$, of an n-sensor array to analyte a is given as the n-dimensional vector containing the mean auto-scaled response of each sensors, $A_{aj}$, to the $a^{th}$ analyte as components such that $$x_a = (A_{a1}, A_{a2}, \ldots A_{an})$$

The average separation, d, between the two analytes, a and b, in the Euclidean sensor response space is then equal to the magnitude of the difference between $x_a$ and $x_b$. The noise of the sensor responses is also important in quantifying the resolving power of the sensor array. Thus the standard deviations, $S_{a,d}$ and $S_{b,d}$, obtained from all the individual array responses to each of a and b along the vector d, are used to describe the average separation and ultimately to define the pairwise resolution factor as $$rf = d_w/(^2_{a,w} + ^2_{b,w})$$

Even if the dimensionality of odor space is fairly small, say on the order of $10^1$, there is still interest in being able to model the biological olfactory system in its construction of arrays consisting of large numbers of receptor sites. Furthermore, even if a relatively small number (<10) of ideal sensors could indeed span odor space, it is not likely that such ideal sensors could be identified. In practice, correlations between the elements of a sensor array will necessitate a much larger number of sensors to successfully distinguish molecules. Furthermore, performance issues such as response time, signal averaging, or calibration ranges may require multiple sensors based on each material. Analysis of regions will add additional degrees of freedom if the components of the region are to be individually identified and will require large numbers of sensors. Fabrication of large numbers of sensors also enables the use of very powerful coherent signal detection algorithms to pull a known, but small amplitude, signal, out of a noisy background. Because of all of these issues, the number of sensors required to successfully span odor space in a practical device may rapidly multiply from the minimum value defined by the dimensionality of smell space.

The approach described herein uses experimental data (e.g. a signal profile, such as a resistance fingerprint) that is generated by an array of differentially responsive sensors. Such sensors include, for example, chemically-sensitive resistor of a sensing array, such as that found in an "electronic nose" as described in U.S. Pat. No. 5,571,401 (the disclosure of which is incorporated herein), when it is exposed to a molecule of interest. The change in the electrical resistance of a chemically-sensitive resistor in such a sensing array can be related to the sorption of a molecule of interest to, for example, the non-conductive regions of the chemically-sensitive resistor. The signals produced by a plurality of chemically-sensitive resistors having individual sorption criteria thus provide information on a number of chemically important properties, such as the hydrophobicity, molecular size, polarity, and hydrogen-bonding interactions of a molecule of interest, thus, for example, creating a resistance profile or fingerprint of the molecule of interest based upon its chemical properties.

By "molecule of interest" or "analyte" is meant any number of various molecules. For example a molecule or analyte of interest may be a nucleic acid (e.g., DNA or RNA), a polypeptide (e.g., an antibody, protein, enzyme), a biochemical (e.g., a lipid, hormone, fatty acids, carbohydrate), pharmaceuticals, a chemical such as organics including, for example, alkanes, alkenes, alkynes, dienes, alicyclic hydrocarbons, arenes, alcohols, ethers, ketones, aldehydes, cyclic hydrocarbons, carbonyls, carbanions, polynuclear aromatics and derivatives of such organics, e.g., halide derivatives.

The analysis of a resistance signal pattern (e.g. a resistance profile) of the embodiment may be implemented in hardware or software, or a combination of both (e.g., programmable logic arrays or digital signal processors). Unless otherwise specified, the algorithms included as part of the invention are not inherently related to any particular computer or other apparatus.

In particular, various general purpose machines may be used with programs written in accordance with the teachings herein, or it may be more convenient to construct more specialized apparatus to perform the operations. However, preferably, the embodiment is implemented in one or more computer programs executing on programmable systems each comprising at least one processor, at least one data storage system (including volatile and non-volatile memory and/or storage elements), at least one input device, and at least one output device. The program code is executed on the processors to perform the functions described herein.

Each such program may be implemented in any desired computer language (including machine, assembly, high level procedural, or object oriented programming languages) to communicate with a computer system. In any case, the language may be a compiled or interpreted language.

Each such computer program is preferably stored on a storage media or device (e.g., ROM, CD-ROM, or magnetic or optical media) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

EXAMPLE

To test the ability of the "electronic nose" to identify molecules of interest having a particular biological activity selected from a library of molecules of interest, a quantitative structure-activity relationship (QSAR) was used to predict the inhibitory action of a series of alcohols on cytochrome P-450 aniline p-hydroxylation.

Polymer synthesis and preparation. Polymers were generally dissolved in tetrahydofuran, except for poly(4-vinylpyridine) and poly(vinylpyrrolidone), which were dissolved in ethanol, and poly(ethylene-co-vinyl acetate)(18% vinylacetate), 1,2-poly(butadiene), and poly(butadiene) (36% cis and 55% trans 1–4), which was dissolved in toluene. Each polymer (160 mg) was dissolved in its respective solvent (20 ml) either at room temperature or by heating to 35–40 C for several hours. Carbon black (40 mg) was added and the suspension sonicated for at least 20 minutes.

Sensor Fabrication. Corning microscope slides were cut into 10 mm×25 mm pieces to provide substrate for the sensor. A 7–8 mm gap across the middle of each piece was masked while 300 nm of chromium and then 500 nm of gold was evaporated onto the ends of the slides to form the electrical contacts. Sensors were formed by spin-coating polymer/carbon black suspensions onto the prepared substrates. The resulting films were then allowed to dry overnight.

Measurements. An automated flow system consisting of LabVIEW software, a pentium computer, and electronically controlled solenoid valves and mass flow controllers were used to produce and deliver selected concentration of solvent vapors to the detectors. To obtain the desired analyte concentration, a stream of carrier gas was passed through a bubbler that had been filled with the solvent of choice. Saturation of the carrier gas with the solvent vapor was verified through measurement of the rate of mass loss of the solvent in the bubbler. The vapor-saturated carrier gas was then diluted with pure carrier gas through the use of mass flow controllers (MKS Instruments, Inc). The carrier gas for all experiments was oil-free air, obtained from the general compressed air laboratory source, containing 1.10+/−0.15 parts-per-thousand (ppth) of water vapor. The air was filtered to remove particulates but deliberately was not dehumidified or otherwise purified to reproduce a range of potential "real world" operating environments. Calibration of the flow system using a flame ionization detector (model 300 HFID, California Analytical instruments, Inc.) Indicated that the delivered analyte concentrations were present.

Eight bubblers for generation of vapors were available, so the 22 alcohols and 2 diols were divided into 3 groups of 8 as indicated in FIG. 5. To precondition the sensors, prior to each of the 3 runs, the sensors were subjected to 40 exposures, 5 to each of the 8 analytes. Data collection then consisted of a set of 10 exposures to the 8 analytes, with 80 exposures performed in randomized order to eliminate systematic errors from history effects. In the third run, bubbler 2 was replaced by a pyrex tube 37 cm in length with a 1 cm inner diameter. This tube was loaded with approximately 25 cm of granular, solid neopentanol. Flow rates were calculated to give 100 ml/min of saturated vapor from the bubblers, which were of sufficient path length to provide saturated vapors. The background air flow was 1900 ml/min, so that the analyte concentration delivered to the sensors was 5% of the analyte's saturated vapor pressure at room temperature. The ability of the vapor delivery system to provide the expected analyte concentrations based on the input and control settings to the mass flow controllers as verified using a calibrated flame ionization detector that sampled several test analyte gas streams being delivered to the sensor chamber.

An exposure had 300 seconds of background air flow, followed by 300 seconds of flow of analyte at 5% of its saturated vapor pressure, followed by 300 seconds of the background air. The DC resistance of each sensor was measured at intervals of approximately 6 seconds using a multiplexing ohmmeter. The baseline resistance of a sensor was taken as an average of all measurements of the resistance of that sensor acquired over a 60 second period that started between 60 and 66 seconds prior to the start of the exposure to an analyte. The exact initiation time of this baseline resistance measurement was different for each sensor, due to small variations in the time interval required to read the set of 20 resistance values through the multiplexing ohmmeter. The resistance response for each sensor to an analyte was taken as an average of all measurements for that sensor in a 60 second period that started between 234 and 240 seconds after the beginning of the presentation of the vapor to the sensors, with the exact initiation time for each sensor channel staggered similarity to that of the baseline resistance readings. A response was taken to be the change in resistance of a sensor, R, divided by its baseline resistance, R. All differential resistance values (R/R) used in the data analysis represented, or very closely approximated, the steady-state resistance readings obtained from the sensors during exposure to the analyte of interest.

Data Analysis. Initial raw data manipulation and calculation of responses was performed using Microsoft Excel. Multiple Linear regression (MLR) was performed using either Excel or the QSAR {Define} module of the Cerius2 program (Molecular Simulations, Inc.) on a Silicon Graphics O2 computer. Many possible MLR models were created, compared, cross-bred, and evolved by the genetic function approximation on Cerius2.

Figure 2:
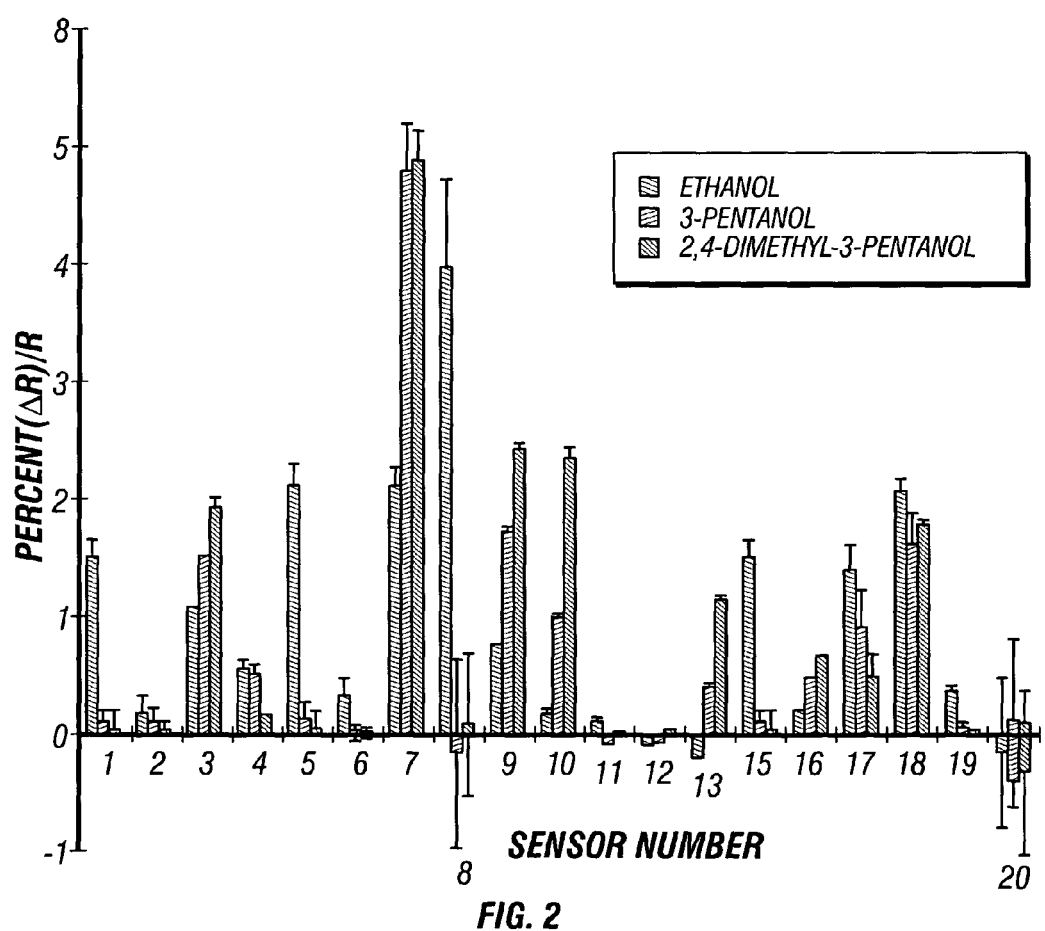
FIG. 2 presents the relative differential resistance responses for various conducting polymer composite sensors to three representative alcohols.

Results. FIG. 2 presents the relative differential resistance responses for various conducting polymer composite sensors to three representative alcohols, and FIG. 5 summarizes all of the sensor response data for the various alcohols investigated in this work. Each alcohol produced a distinct, characteristic response pattern with the array of sensors chosen for use in the work. Other sensor arrays comprising different polymer formulatives are clearly capable of providing response patterns useful in the present invention.

The responses of the 19 working sensors to 20 of the alcohols (FIG. 5) were used to build a QSAR model. Benzyl alcohol and tert-amyl alcohol were excluded from the fit because their biological activities were anomalous. The two diols were also excluded while building the model.

The inhibitory action data of Cohen and Mannering (Mol. Pharmacol. 1973, 9, 383–397) are listed in FIG. 5. The values are expressed as $pI_{50}$, where $I_{50}$ is the concentration of the alcohol (in mM) at which the activity of the enzyme is 50% inhibited, and $pI_{50}$ is the negative logarithm of $I_{50}$. More positive numbers correspond to more strongly inhibiting alcohols.

The QSAR equations consist of a linear combination of descriptors whose coefficients are obtained by a least-squares fitting of predicted to observed biological activity through multiple linear regression. Equation 1 represents a general set of QSAR equations, $$A \cdot X_{1,1} + B \cdot X_{1,2} + C \cdot X_{1,3} + \ldots + J \cdot X_{1,n} + K = Y_1 \quad (1a)$$

$$A \cdot X_{2,1} + B \cdot X_{2,2} + C \cdot X_{2,3} + \ldots + J \cdot X_{2,n} + K = Y_2 \quad (1b)$$

$$A \cdot X_{m,1} + B \cdot X_{m,2} + C \cdot X_{m,3} + \ldots + J \cdot X_{m,n} + K = Y_m \quad (1m)$$

where $Y_i$ is the biological activity of the $i^{th}$ molecule, $X_{i,j}$ is the value of the $j^{th}$ descriptor for the ith molecule, and A, B, C, ... K are constants that are obtained through the fitting of $Y_i$ (predicted) versus $Y_i$ (observed). In Equation 1, the $i^{th}$ alcohol's inhibitory activity is represented by $Y_i$ and its n sensor responses are taken as its descriptors ($X_{i,1}$ to $X_{i,n}$).

The genetic function algorithm of the QSAR module of Cerius2 was used to select the best sensors for the QSAR. One hundred multiple linear regression models were generated from random combinations of 4 sensors. These models were ranked according to a lack-of-fit (LOF) parameter, as given by equation 2:

$$LOF = \frac{LSE}{(1 - ((c + dp)/m))\hat{\ }2} \quad (2)$$

LSE is the least-squares error, c and p are both the number of descriptors (sets of relative differential resistance response of the sensors in the array) for a simple linear model such as the one herein, M is the number of samples (e.g., alcohols), and d is the "smoothing parameter", which is entered by the user (1.0 was used). The LOF value is therefore an inverse measure of how well the model fits the data, with a penalty for the use of a large number of descriptors relative to samples. From the set of 100 models, two "parents" are chosen, with a probability inversely proportional to their LOF, and "crossed over"—some of the descriptors from each are used to form a new model. There is then a probability for "mutation", where a new, randomly chosen, descriptor is added to the "daughter". If the daughter is not already present in the population, it replaces the model with the worst LOF from the population. After 5,000 rounds of genetic operation, convergence is generally reached, in which the optimal models have been found.

When the 19 sets of responses from the working sensors were given to the Genetic Function Algorithm (GFA), a model that incorporated 5 of the sensors was found to be optimal. The best fit is described by equation 3:

$$pI_{50} = 0.51\text{-}3 + 1.90\text{-}9 - 3.58\text{-}13 - 2.14\text{-}15 - 0.90\text{-}18 - 1.29 \quad (3)$$

n=20 R=0.995 s=0.092 F=297

Figure 3:
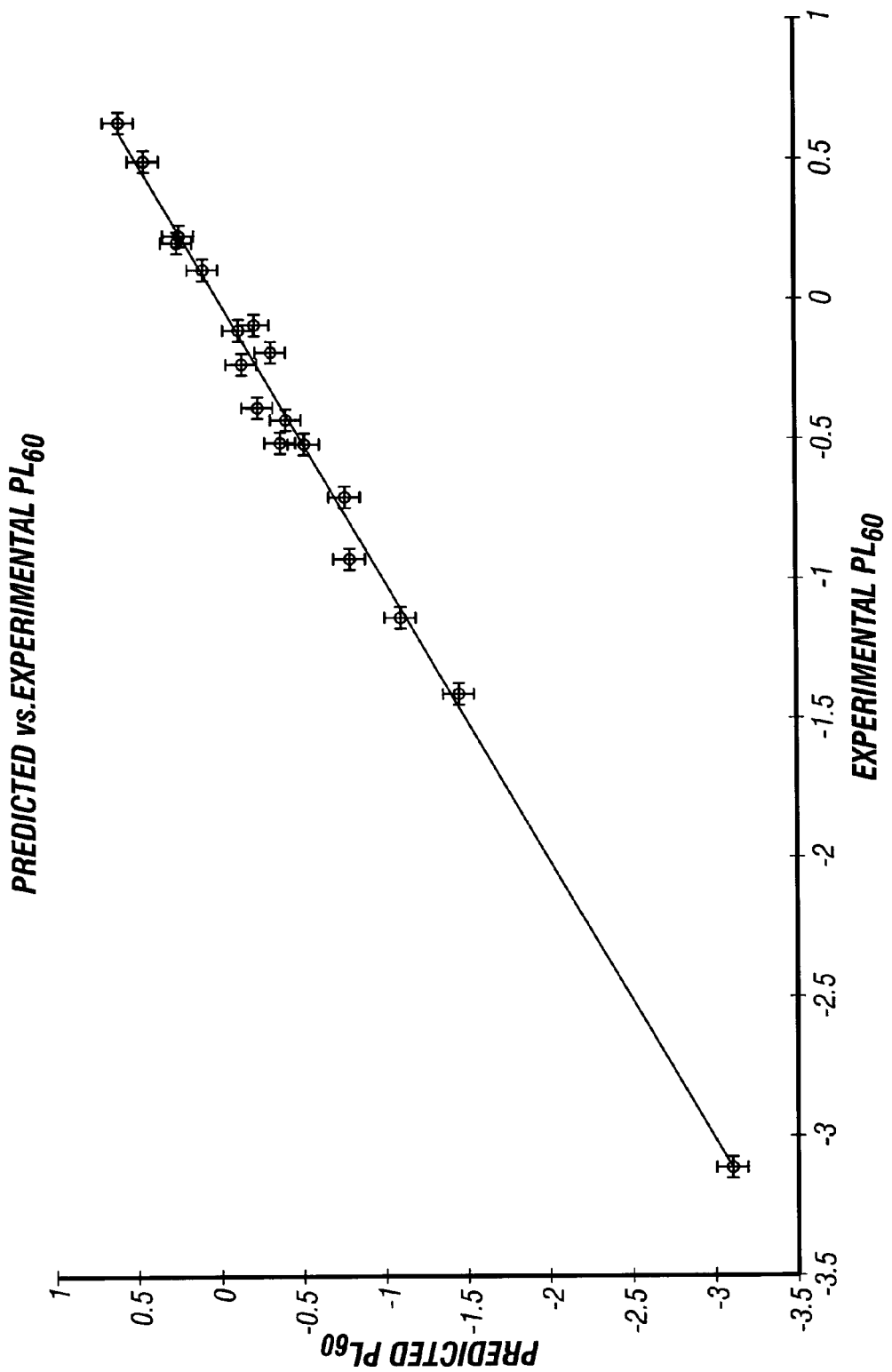
FIG. 3 shows a plot of $pI_{50}$ predicted by equation 3 versus the actual experimental value. Horizontal error bars represents an average experimental error and vertical error bars correspond to the standard error of equation 3. The line represents perfect agreement between experiment and prediction.
Figure 4:
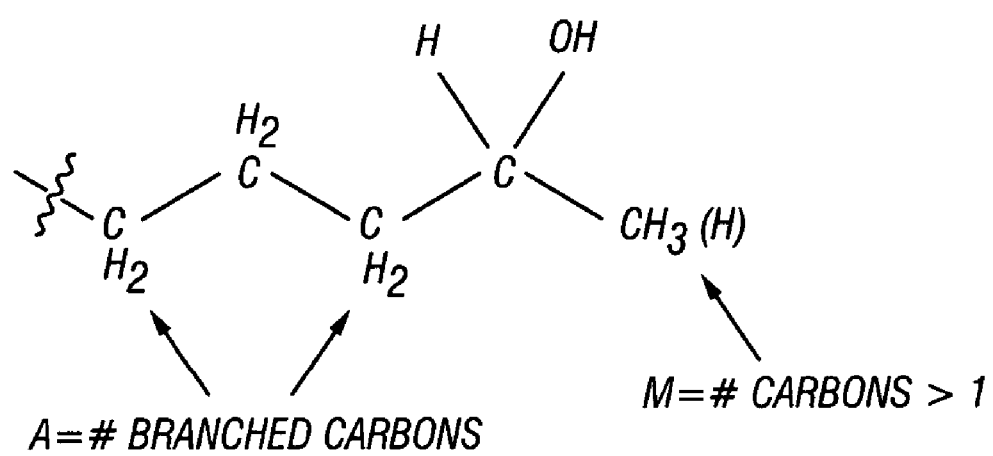
FIG. 4 shows a diagram illustrating the M and A steric parameters.

The numbers in bold refer to sets of responses from the sensors with those numbers, n is the number of samples, R is the correlation coefficient, and s is the standard error. The correlation coefficient of 0.995 indicates that the fit was quite good. The F statistic of 297 indicates that the overall significance of the fit is very high, in fact is at a level of $1$-$10^{-13}$. Coefficients for all sensors are significant far beyond the 99.9% level, as attested to by their t statistics (see table 3). Predicted versus experimental $pI_{50}$ values are plotted in FIG. 3.

TABLE 3

Regression Statistics For the Coefficients of Equation 3

| | Coefficient | Standard Error | t Stat | P-value |
|---|---|---|---|---|
| Intercept | −1.29 | 0.27 | −4.71 | 3.32E−04 |
| 3 | 0.51 | 0.07 | 6.93 | 6.98E−06 |
| 9 | 1.90 | 0.19 | 9.92 | 1.03E−07 |
| 13 | −3.58 | 0.21 | −17.13 | 8.70E−11 |
| 15 | −2.14 | 0.27 | −7.91 | 1.56E−06 |
| 18 | −0.90 | 0.08 | −11.34 | 1.94E−08 |

The t statistic is equal to the value of the coefficient divided by its standard error; it is used to derive the P value, which indicates the significance of the coefficient.

Methanol has an inhibition activity distinctly different from that of the other alcohols, and this can lead to a misleadingly good fit through a "point and cluster" effect. A second least-squares fitting of equation 3 was performed with the exclusion of methanol. The coefficient of 15 changed from −2.14 to −2.20, while those of the other sensors remained nearly the same. The overall quality of the fit declined; F decreased from 297 to 109, corresponding to a decrease in the significance of the fit from the level of $1$-$(1 \times 10^{-13})$ to $1$-$(4 \times 10^{-10})$. The decrease quality of the fit occurs because methanol is modeled well by the equation, but when methanol is excluded there is much less variation in the data to be fit.

Electronic Nose-Based QSAR. The selection of which molecules to include in a QSAR is crucial. In the sense, that it is desirable to use the broadest set of molecules available to build a QSAR, while not including only one or two molecules from a distinctly different class of compounds. For example, benzyl alcohol, the only aromatic alcohol in the data set, has a higher activity than is predicted by both our QSAR and another QSAR on the cytochrome P-450 system. The anomalous activity of benzyl alcohol could be accounted for with an additional descriptor unique to benzyl alcohol, but the choice of such a parameter is rather arbitrary, so benzyl alcohol was excluded during the building of our QSAR. Tert-amyl alcohol was also excluded because there is evidence that tertiary alcohols function through a stimulatory mechanism in addition to the usual inhibitory mechanism. As would be expected in tert-amyl alcohol were also acting through this stimulatory mechanism, its inhibitory activity is anomalously low. The two diols were also excluded while building the model. Because of these limitations, the QSAR is expected to be most successful at predicting the activity of aliphatic mono-alcohols having no other functionalities.

The sensors chosen for the model by the GFA are among those whose responses are most reproducible. Reproducibility was measured by examining the set of 10 response of a given sensor to a given analyte. The value $S_{i,j}$ is defined as the standard deviation among the 10 responses of the $j^{th}$ sensor to the $i^{th}$ alcohol divided by the average of those responses. Each sensor has a set of 20 S values, one for each alcohol. A sensor's reproducibility can be gauged by the median of its set of S values. Four of the five sensors used in the model displayed median S values less than 0.063, raking them among the best seven sensors. The only sensor outside this group, 15, responded only to very polar analytes. Since its response to the majority of the analytes was quite small, its S value for those analytes is very large. However, for the analytes to which it did respond, for example methanol and ethanol, its S values are small, 0.040 and 0.041, respectively. The inclusion of 15 might be questioned if it were necessary only to model the activity of one analyte, namely the outlier methanol. To test the validity of including 15 in the QSAR, equation 3 was refit with the same set of sensors and all of the previously used alcohols, excluding methanol. In the new QSAR, the significance of 15 remains significant. If the set of five sensor responses to methanol are substituted into the second QSAR equation, which was formed with no information about methanol, the predicted $pI_{50}$ of methanol is −3.12 very close to its experimental value of −3.09. It appears that whatever molecular characteristics are probed by 15 are successfully extrapolated from the more moderately polar analytes to methanol. In other words, 15 is not just an indicator variable for methanol that is fit with an arbitrary coefficient.

A quantitative measure of the predictive power of the QSAR can be obtained by building a model using the biological and sensor response data from all the molecules except one, and then predicting the activity of the excluded molecule with that model. The procedure is repeated for each molecule in the data set, and the predictive sum of squares (PRESS) is defined as the sum, over all analytes, of the squared differences between the predicted and actual biological activity. Using equation 3, the PRESS for the set of 20 alcohols is 0.221. This value can be compared to the residual sum of squares, RSS, in which one QSAR equation (fit to all samples) is used to calculate the predicted activity. As would be expected, the RSS of 0.117 is lower than the PRESS. More significantly, a large difference between the PRESS and RSS would imply that the model had used too many parameters and overfit the data, and this appears not to be the case.

An optimum fit (as judged by the LOF parameter) was found to require five descriptors; no equation with a different number of descriptors formed as significant a model. The best 4 sensors QSAR, consisting of sensors 1, 13, 16 and 17, has an R=0.984, s=0.163, and F=114, indicating an overall significance at the level of $1-(5 \times 10^{-11})$. On the other hand, addition of further sensors adds parameters and enables a better fit to the data set. However, if 4 is added to equation 3 to form the best 6-sensor equation, certain key statistics point to a diminished model. As would be expected with an additional parameter, R increases, from 0.995 to 0.996. Additionally, the standard error decreases from 0.0916 to 0.0834, the RSS decreases from 0.117 to 0.090, and the F statistic increases from 297 to 300. However, the significance of the fit, represented by the F statistic, decreases from $1-(1.08 \times 10^{-13})$ to $1-(3.66 \times 10^{-13})$. The PRESS increases from 0.221 to 0.253. Thus, although the 6-sensor model fits the set of 20 alcohols better than the 5-sensor model, the 6-sensor model is worse at predicting the activity of an alcohol that was not included in the fit, indicating that the 6-sensor model has overfit the data.

As described above, the cytochrome P-450 p-hydroxylation inhibition activities of all the aliphatic mono-alcohols investigated in this work could be quite accurately predicted from a model that was constructed without the use of any information about the molecular structure of the alcohols for which the prediction are made. This indicates that the resistance data output of the electronic nose contains implicit information on most of the chemical factors that control the interactions of the enzyme with the alcohols. These resistance data reflect the binding interactions between the alcohols and a collection of polymers having a diverse collection of chemical attributes. It is not necessary that an individual polymer probe specifically and exclusively one such descriptor of the analyte-substrate interaction, because the desired information can be obtained through analysis of the collective response of the sensor array to an analyte.

Comparison with Other QSARs. Cohen and Mannering fit the activity of 11 of the unbranched 1- and 2-alcohols (excluding methanol) to a one parameter equation using log P (J. Mol. Pharmaco. 1973, 9, 383–397). A modified version, using updated log P values and fit to only 10 alcohols (excluding methanol and ethanol), was given later by Shusterman (equation 4) (Chem.-Biol. Interactions 1990, 74, 63–77).

$$pI50 = 0.43 \log P - 0.53 \quad (4)$$

N=10 R=0.954 s=0.128

However, Shusterman also showed that for a larger set of alcohols, a simple fit to log P was inadequate to describe most of their activity; a fit of 19 alcohols yielded equation 5, which has rather poor regression statistics.

$$pI50 = 0.35 \log P - 0.71 \quad (5)$$

n=19 R=0.505 s=0.468

In a second equation using two descriptors, log P and (log p)^2, Cohen and Mannering fit 17 of the alcohols with an R of 0.98 (equation 6).

$$pI50 = 1.50 \log p - 0.36 (\log P)^2 + 1.75$$

n=17 R=0.98 s=0.44

Although this was a better fit, it used more descriptors. Additionally, it is evident from inspection of the data that there are factors besides hydrophobicity that determine an alcohol's activity. Four subsequent QSARs have therefore been used to model; the data set more fully and some aspects of these models are discussed below.

A more complex, three parameter, QSAR was based upon log P, a calculated electronic parameter ($_{HOMO}$), and a steric parameter (BULK$_{lat}$)(equation 7).

$$pI_{50} = 16.2 \log P - 16.0 \log(P+1) - 1.35 \text{BULK}_{lat} + 0.381_{HOMO} + 22.5 \quad (7)$$

n=21 R=0.982 s=0.170 log=1.05

Shusterman and Johnson, however, pointed out that the use Of HOMO as a parameter was unjustified since it was necessary only to fit benzyl alcohol, and becomes an insignificant parameter (as indicated by its t value) when benzyl alcohol is excluded from the data set. Similarly, the bilinear dependence of pI50 upon log P of equation 7 was necessary only to fit a single data point, methanol.

Another QSAR, based on a choice of molecular connectivity indices, has also been used to model the activity of 20 alcohols (benzyl alcohol and tert-amyl alcohol were excluded (equation 8).

$$pI50 = -6.88(1/^{o\nu}) - 1.14^{4}{}_{PC} + 1.85 \quad (8)$$

n=20 R=0.983 s=0.156

The parameter $^{o}{}^{\nu}$, the zero-order valence molecular connectivity index, basically corresponds to molecular size, and therefore hydrophobicity, for this set of molecules. Hence, the inverse of the index has a negative coefficient in equation 8. The parameter $^{4}{}_{PC}$, the fourth-order path/cluster molecular connectivity index, correlates with the degree of branching in the molecule, and therefore also has a negative coefficient in equation 8.

A third QSAR, which relies entirely upon calculated electronic parameters as descriptors, has been constructed and used to fit all 22 alcohols. Shusterman noted problems with the QSAR. For example, it was asserted that the -carbon of the alcohols was acting as an electron acceptor from the enzyme, because a correlation between activity and QCL, the electron density on the -carbon in the LUMO, was found. QCL is correlated with log P(R=0.747), to some extent explaining the fit. Two alcohols, 3-methylbutanol and 2,4-dimethyl-3-pentanol, were poorly fit, and no rationalization was presented for why the correlation with QCL would not apply to these two substrates as well.

Finally, Shusterman created a QSAR based on log P and two steric parameters, M and A, which were used to describe the branching of the alcohols. M is the number of carbons beyond the methyl substituent in FIG. 3, thus, 1- and 2-alcohols have an M=0, while M for 3-pentanol would be one, and for 2,4-dimethyl-3-pentanol is 2. The second parameter, A, refers to the number of branched carbons in the main chain, A=1 for 2-methyl-1-butanol and 2 for neopenyl alcohol. A fit of 19 of the alcohols (benzyl alcohol, tert-amyl alcohol, and methanol were excluded) yielded equation 9. The negative coefficient for M and A indicate the loss of activity with branching.

$$pI50 = 0.48 \log P - 0.65 \cdot M - 0.31 \cdot A - 0.60 \quad (9)$$

n=19 R=0.955 s=0.171

To compare the electronic nose QSAR to those of Sabljic and Shusterman, one must use statistics that take into account the number of descriptors used. Table 5 lists the comparison of selected regression statistics from the QSAR of Sabljic, Shusterman, equation 3, and the QSAR created when the coefficients of equation 3 were fit to the 19 alcohols besides methanol (R is the correlation coefficient, s is the standard error, and the final column is the overall significance of the regression equation). Because the electronic nose QSAR model uses more parameters, it is inappropriate to compare just either the correlation coefficients, standard error, or residual sum of squares of the models. To some extent, the PRESS should be independent of the number of parameters in a model, since the model is tested upon molecules about which it has no information. The PRESS of the electronic nose QSAR model is significantly lower than the other two models of interest. Finally, the F steatitic gauges the overall significance of the fit while accounting for the number of parameters used. By this measure, the electronic nose QSAR is approximately as significant as Sabljic's and more significant than Shusterman's.

TABLE 5

| | Data pts fit | descriptors used | R | s | RSS | PRESS | F | Significance F |
|---|---|---|---|---|---|---|---|---|
| Sabljic | 20 | 2 | 0.983 | 0.156 | 0.414 | 0.872 | 250 | 2.51E−13 |
| Shusterman | 19 | 3 | 0.956 | 0.17 | 0.436 | 0.786 | 53 | 3.34E−08 |
| Present Disclosure | 20 | 5 | 0.995 | 0.092 | 0.117 | 0.221 | 297 | 1.08E−13 |
| Present Disclosure (no methanol) | 19 | 5 | 0.988 | 0.095 | 0.117 | 0.243 | 109 | 3.89E−10 |

It appears that the important chemical interaction involved in the partitioning of the aliphatic alcohols into the enzyme binding site are probed by the array responses. The construction of our QSAR did not require making assumption regarding which steric or electronic factors are important or what parameters to use to capture such effects.

Obtaining chemical insight into the nature of the dominant binding forces involved in the reaction being modeled would require a complete understanding of the chemical factors that determine the analyte partitioning into each polymer in the electronic nose. In principle it is possible to extract such information for certain descriptors of interest, but it is not necessary to have such information in order to use the readily-obtained electronic nose data to predict successfully the activity of various alcohols in inhibiting cytochrome P-450 activity.

Materials

This example illustrates the use of an array of conductive/non-conductive region sensors. In this example, carbon black is the conductive region material. The carbon black (Black Pearls 2000) is a furnace black material from Cabot Co. (Billerica, Mass.). The nonconductive region comprises a nonconductive polymer.

To prepare the detector substrates, two parallel bands of gold, 50–100 nm thick and separated by 5 mm, are deposited onto conventional 7.5 cm×2.5 cm glass slides. The slides are then cut into strips to produce 0.7 cm×2.5 cm pieces of glass, with each strip of glass having one pair of Au leads spaced 5 mm apart.

The detectors are made from a solution of polymer into which carbon black has been suspended. In this example, 125 mg of the polymer is dissolved in 10 mL of tetrahydrofuran, and carbon black (42 mg) is then suspended in this solution, to produce a composition of 75% polymer and 25% carbon black by weight of solids. One coating of this suspension is applied to each substrate yielding a film thickness of ≈1 micron as can be determined by atomic force microscopy. For larger sensor thicknesses, more coats are used.

Methods

The dc resistance of each detector is determined as a function of time using a simple two-point resistance configuration. Contacts are made to the gold lines by pressure-contacting electrical leads using flat-jawed alligator clips. Resistance data is acquired using a Hydra 2620A Data Acquisition Unit (John Fluke Mfg. Co.; Everett, Wash.), which is interfaced to a personal computer. All of the films had resistance values below the 10 MΩ limit of the Hydra 2620A.

To initiate an experiment, five copies of a given detector type are placed into the glass chamber and a background flow of nitrogen is introduced until the resistance of the detectors is stabilized. Solvent vapor streams are then passed over the detectors. The background and analyte flow rates are monitored using two flow meters (Gilmont Instruments, Inc.) which have limits of 0.2 L min$^{-1}$ to 15.0 L min$^{-1}$ and 0.0015 L min$^{-1}$ to 0.310 L min$^{-1}$, respectively. In a typical experiment, resistance data on the detectors are collected for 150 s with just the background gas flowing (typically about 1–2 L min$^{-1}$) to serve as a baseline. This is followed by a 10 s to 2 minutes data collection while the detectors are exposed to the analyte vapor stream (typically about 200–300 mL min$^{-1}$). The detectors are then given 200–300 s to recover during which pure background gas was passed through the chamber. The exposure times varied, but steady state values of resistance change are always reached for any given exposure time. Resistances for all detectors in a given trial were monitored contemporaneously through the use of the multiplexing capabilities of the Hydra voltmeter. Results are obtained by running two trials of five exposures each, with the trials performed on different days. Each analyte is exposed to five copies of the detector simultaneously and the results.

This example illustrates a response of an array of sensors having predetermined polymer thicknesses of 100 nm and 500 nm to an analyte.

With reference to FIG. 6, a response of an array of detectors having predetermined polymer thicknesses of 100 nm and 500 nm to an analyte is illustrated. In this example, the polymer used was polycaprolactone and the analyte used was benzophenone. All the detectors displayed an increase in resistance upon exposure to the vapor, and returned to their baseline values after the vapor was removed. The change in resistance for the thinnest polymer showed steady-state conditions faster compared to the thickest sensor which reach steady-state conditions at a slower pace. The responses are analyzed by calculating the maximum differential response value, $\Delta R_{max}$, observed during the exposure period and dividing it by the baseline value of the resistance, $R_i$, (taken as the resistance value just before the exposure began) and expressed as:

$$\Delta R_{max}/R_i \qquad \text{Equation III}$$

A plot of the response flux as a function of time can be used to calculate a diffusion coefficient. In order to measure the diffusivity experimentally in a polymer based sensor, the time lag procedure is used. The time lag θ is estimated from the time axis intercept and the diffusion coefficient is obtained using Equation II.

This example illustrates a response of an array of detectors having predetermined polymer thicknesses and analytes having different volatilities.

Figure 7:
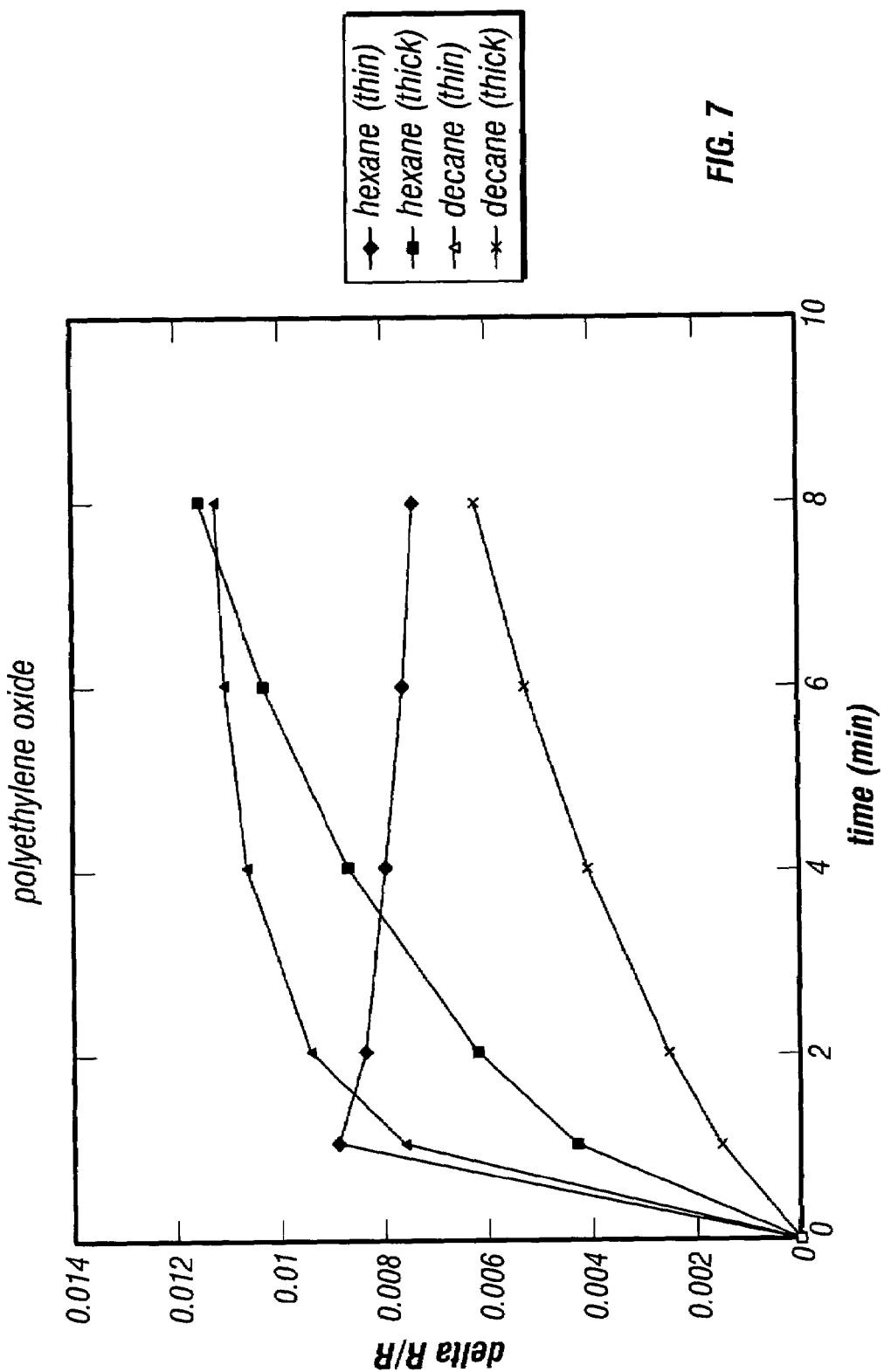
FIG. 7 illustrates various responses as a function of sensor thickness and analyte volatility.

With reference to FIG. 7, the responses of an array of detectors having predetermined polymer thicknesses (one thin, one thick) and to different analytes is illustrated. The polymer used was polyethylene oxide and the analytes were hexane and decane. The results indicate that the thin sensor shows steady-state conditions faster compared to the thick sensor which reaches steady state conditions at a slower pace. In addition, the analyte that is more volatile, (hexane), reaches steady-state conditions faster than an analyte that is less volatile (decane). Table 1 shows the responses of the thin and thick sensors versus time as well as the responses of two different analytes.

TABLE 5

| | Time (min) | | | | |
|---|---|---|---|---|---|
| | 1 | 2 | 4 | 6 | 8 |
| Hexane (thin) | 0.008917 | 0.008389 | 0.007985 | 0.007678 | 0.007468 |
| Hexane (thick) | 0.00428 | 0.0062 | 0.008713 | 0.010352 | 0.011586 |
| Decane (thin) | 0.007624 | 0.009453 | 0.010664 | 0.011088 | 0.011286 |
| Decane (thick) | 0.001577 | 0.002578 | 0.004103 | 0.00529 | 0.006279 |

By monitoring the temporal response lag between different film thicknesses to a response, sensors having advantageous features are realized. For example, when monitoring certain volitilities components, the lag time is an important component which can be monitored. False rates can be minimized if the lag profile does not correspond to the expected lag profile.

Although only a few embodiments have been described in detail above, those having ordinary skill in the art will certainly understand that many modifications are possible in the preferred embodiment without departing from the teachings thereof. All such modifications are intended to be encompassed within the following claims.

What is claimed is:

1. A plurality of sensors comprising:
a first conductive material and a second compositionally different material, wherein at least one sensor comprises a different thickness than at least one other sensor of the plurality of sensors such that each sensor of the plurality of sensors comprises regions of a first conductive material and regions of a second material compositionally different than the first material, the plurality of sensors made by a process comprising:
spraying a plurality of substrates, each having at least two conductive leads, with a suspension between the at least two conductive leads, and wherein at least one substrate receives more suspension that at least one other substrate.

2. The plurality of sensor of claim 1, wherein the suspension is applied to the substrates with an airbrush.

3. The plurality of sensors of claim 2, wherein the airbrush is fitted with a nozzle that sprays in a desired geometry.

4. The plurality of sensors of claim 1, wherein the first material is selected from the group consisting of Ag, Au, Cu, Pt, carbon black, and AuCu, and the second material compositionally different than the first material is selected form the group consisting of a non-conductive material, a semi-conductive material, a conductive organic material, wherein the conductive organic material is selected form the group consisting of a polyaniline, an emeraldine salt of polyaniline, a polypyrrole, a polythiophene, and a polyEDOT.

5. A plurality of sensor comprising a first conductive material and a second compositionally different material, wherein at least one sensor comprises a different thickness than at least one other sensor of the plurality of sensors such that each sensor of the plurality of sensors comprises regions of a first conductive material and regions of a second material compositionally different than the first material, the plurality of sensors made by a process comprising:
spraying a substrate, comprising at least 2 pair of conductive leads, with a suspension between the at least 2 pair of conductive leads wherein at least one area of the substrate receives more suspension that at least one other area of the substrate thereby forming at least 2 sensors of different thickness.

* * * * *